US006379398B1

(12) United States Patent
Genet et al.

(10) Patent No.: US 6,379,398 B1
(45) Date of Patent: Apr. 30, 2002

(54) CATIONIC COMPOUNDS, THEIR USE FOR THE OXIDATION DYEING OF KERATIN FIBRES, DYE COMPOSITIONS AND DYEING PROCESSES

(75) Inventors: Alain Genet, Aulnay sous Bois; Alain Lagrange, Coupvray, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/387,508

(22) Filed: Sep. 1, 1999

(30) Foreign Application Priority Data

Sep. 2, 1998 (FR) .............................. 98 10977

(51) Int. Cl.$^7$ ..................... D61K 7/13; C07C 211/00; C07D 233/58
(52) U.S. Cl. .................. 8/409; 8/416; 8/426; 8/654; 8/423; 8/655; 564/282; 564/290; 548/314.4; 548/335.5; 548/346.1
(58) Field of Search .................. 8/406, 408, 416, 8/426, 606, 654, 409, 423, 573, 655; 564/282, 290; 548/314.4, 335.5, 346.1

(56) References Cited

U.S. PATENT DOCUMENTS

| 3,622,629 | A | * | 11/1971 | Lugosy ........................ 564/287 |
| 4,581,370 | A | * | 4/1986 | Diamond et al. ......... 548/335.5 |
| 4,888,025 | A | * | 12/1989 | Bugaut et al. ................. 8/405 |
| 5,139,532 | A | | 8/1992 | Chan et al. ..................... 8/405 |
| 5,169,403 | A | | 12/1992 | Chan et al. ..................... 8/405 |
| 6,024,768 | A | * | 2/2000 | Bittner et al. .................. 8/410 |

FOREIGN PATENT DOCUMENTS

| FR | 2 520 358 | | 7/1983 |
| FR | 2 586 913 | | 3/1987 |
| FR | 2 766 178 | | 1/1999 |
| GB | 2 129 022 | | 5/1984 |
| WO | 98/01418 | * | 1/1998 |
| WO | WO 99/03819 | | 1/1999 |

OTHER PUBLICATIONS

J.F. Corbett, "Recent Developments in the Synthesis of Hair Dyes", Journal of the Society of Dyers and Colourists, vol. 84, Nov. 1968, pp. 556–557.
Ortho Diamino–Benzenes Avec Azote Extra–Nucleaire Quaternise, pp. 9–11, Jan. 1999.
English language Derwent Abstract of FR 2 520 358, Jul. 1983.
English language Derwent Abstract of FR 2 586 913, Mar. 1987.
English language Derwent Abstract of FR 2 766 178, Jan. 1999.

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

Dibenzenic ortho-phenylenediamines comprising at least one cationic group Z, Z being chosen from quaternized aliphatic chains, aliphatic chains comprising at least one quaternized saturated ring, and aliphatic chains comprising at least one quaternized unsaturated ring, to their use as oxidation base, coupler or autooxidizable dye for the oxidation dyeing of keratin fibers, to dye compositions containing them, and to oxidation dyeing processes using them.

31 Claims, No Drawings

CATIONIC COMPOUNDS, THEIR USE FOR THE OXIDATION DYEING OF KERATIN FIBRES, DYE COMPOSITIONS AND DYEING PROCESSES

The invention relates to dibenzenic ortho-phenylenediamines comprising at least one cationic group Z, Z being chosen from quaternized aliphatic chains, aliphatic chains comprising at least one quaternized saturated ring, and aliphatic chains comprising at least one quaternized unsaturated ring, to their use for the oxidation dyeing of keratin fibres, to dye compositions containing them, and to oxidation dyeing processes using them.

It is known practice to dye keratin fibres, and in particular human hair, with dye compositions containing oxidation dye precursors, in particular para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

Oxidation dyes, by which so-called "permanent" coloration can be obtained, must satisfy a certain number of requirements. Oxidation dyes should have no toxicological drawbacks, should allow shades of the desired strength to be obtained, and should have good resistance to external agents (e.g., light, bad weather, washing, permanent-waving, perspiration and friction).

The dyes should also allow white hairs to be covered, and should be as unselective as possible, i.e. they should allow the smallest possible differences in coloration to be produced over the entire length of the same keratin fibre, which may indeed be differently sensitized (i.e. damaged) between its tip and its root.

The inventors have discovered, surprisingly and unexpectedly, that a novel family of dibenzenic ortho-phenylenediamines of formula (I) defined below, comprising at least one cationic group Z, Z being chosen from quaternized aliphatic chains, aliphatic chains comprising at least one quaternized saturated ring, and aliphatic chains comprising at least one quaternized unsaturated ring, are suitable for use as oxidation bases or as couplers or as self-oxidizing compounds for oxidation dyeing, and can also allow dye compositions to be obtained which can lead to strong colorations, in a wide range of shades, and which can have excellent properties of resistance to the various treatments to which keratin fibres may be subjected. These compositions can be readily synthesized.

These discoveries form the basis of the present invention.

A subject of the invention is thus ortho-phenylenediamines of formula (I) below, and the acid addition salts thereof:

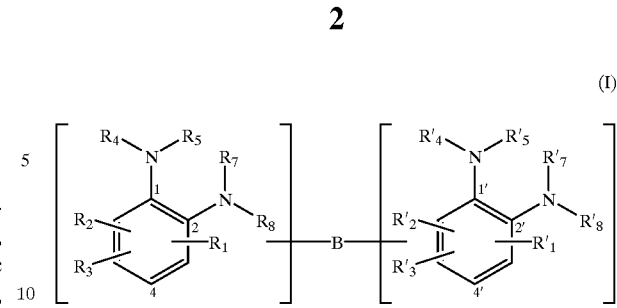

(I)

in which:
B is a linker arm chosen from linear and branched alkyl chains, which can be optionally interrupted with at least one group chosen from Z groups and hetero atoms such as oxygen, sulphur, and nitrogen, and which can be optionally substituted with at least one substituent chosen from hydroxyls and ($C_1$–$C_6$) alkoxys, and which can optionally bear at least one ketone function; in an embodiment of the invention, the alkyl chains comprise from 1 to 14 carbon atoms;

$R_1$, $R_2$, $R_3$, $R'_1$, $R'_2$ and $R'_3$, which may be identical or different, can be the point of attachment of a linker arm B, i.e., they represent one of the two valencies of linker arm B; otherwise, they are chosen from a hydrogen atom; halogens; Z groups; ($C_1$–$C_6$)alkylcarbonyls; amino($C_1$–$C_6$)alkylcarbonyls; N—Z-amino($C_1$–$C_6$)-alkylcarbonyls; N—($C_1$–$C_6$)alkylamino($C_1$–$C_6$) alkylcarbonyls; N,N-di($C_1$–$C_6$)alkylamino($C_1$–$C_6$) alkylcarbonyls; amino($C_1$–$C_6$)alkylcarbonyl($C_1$–$C_6$) alkyls; N—Z-amino($C_1$–$C_6$)alkylcarbonyl($C_1$–$C_6$) alkyls; N—($C_1$–$C_6$)alkylamino($C_1$–$C_6$)-alkylcarbonyl ($C_1$–$C_6$)alkyls; N,N-di($C_1$–$C_6$)alkylamino($C_1$–$C_6$) alkylcarbonyl-($C_1$–$C_6$)alkyls; carboxyl; $C_1$–$C_6$ alkylcarboxyls; ($C_1$–$C_6$)alkylsulphonyls; aminosulphonyls; N—Z-aminosulphonyls; ($C_1$–$C_6$)N-alkylaminosulphonyls; N,N-di($C_1$–$C_6$) alkylaminosulphonyls; ($C_1$–$C_6$)aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; carbamyl; N—($C_1$–$C_6$)alkylcarbamyls; N,N-di($C_1$–$C_6$) alkylcarbamyls; carbamyl($C_1$–$C_6$)alkyls; N—($C_1$–$C_6$) alkylcarbamyl($C_1$–$C_6$)alkyls; N,N-di($C_1$–$C_6$) alkylcarbamyl($C_1$–$C_6$)alkyls; ($C_1$–$C_6$)alkyls; ($C_1$–$C_6$) monohydroxyalkyls; ($C_2$–$C_6$)polyhydroxyalkyls; ($C_1$–$C_6$)alkoxy($C_1$–$C_6$)alkyls; ($C_1$–$C_6$)trifluoroalkyls; cyano; $OR_6$ and $SR_6$ groups; amino groups protected with a radical chosen from ($C_1$–$C_6$)alkylcarbonyls, ($C_1$–$C_6$)alkylcarboxyls, trifluoro($C_1$–$C_6$) alkylcarbonyls, amino($C_1$–$C_6$)alkylcarbonyls, N—Z-amino($C_1$–$C_6$)alkylcarbonyls, N—($C_1$–$C_6$)alkylamino ($C_1$–$C_6$)alkylcarbonyls, N,N-di($C_1$–$C_6$)alkylamino ($C_1$–$C_6$)alkylcarbonyls, ($C_1$–$C_6$)alkylcarboxyls, carbamyl, N—($C_1$–$C_6$)alkylcarbamyls, N,N-di($C_1$–$C_6$) alkylcarbamyls, ($C_1$–$C_6$)alkylsulphonyls, aminosulphonyls, N—Z-aminosulphonyls, ($C_1$–$C_6$)N-alkylaminosulphonyl, N,N-di($C_1$–$C_6$) alkylaminosulphonyls, thiocarbamyl, formyl, and Z groups in which the linker arm B comprises a ketone function directly attached to the nitrogen atom of the amino group;

$R_6$ can be the point of attachment of a linker arm B, i.e., it can be one of the two valencies of a linker arm; otherwise $R_6$ is a radical chosen from ($C_1$–$C_6$)alkyls; ($C_1$–$C_6$)monohydroxyalkyls; ($C_2$–$C_6$)

polyhydroxyalkyls; Z groups; $(C_1-C_6)$alkoxy$(C_1-C_6)$ alkyls; aryls; benzyl; carboxy$(C_1-C_6)$alkyls; $(C_1-C_6)$ alkylcarboxy$(C_1-C_6)$alkyls; cyano$(C_1-C_6)$alkyls; carbamyl$(C_1-C_6)$alkyls; N—$(C_1-C_6)$alkylcarbamyl $(C_1-C_6)$alkyls; N,N-di$(C_1-C_6)$alkylcarbamyl$(C_1-C_6)$ alkyls; $(C_1-C_6)$trifluoroalkyls; $(C_1-C_6)$ aminosulphonylalkyls; $(C_1-C_6)$N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; $(C_1-C_6)$ alkylsulphinyl$(C_1-C_6)$alkyls; $(C_1-C_6)$alkylsulphonyl-$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two identical or different radicals chosen from $(C_1-C_6)$alkyls, $(C_1-C_6)$ monohydroxyalkyls, $(C_2-C_6)$polyhydroxyalkyls, $(C_1-C_6)$alkylcarbonyls, formyl, trifluoro-$(C_1-C_6)$ alkylcarbonyls, $(C_1-C_6)$alkylcarboxyls, carbamyl, N—$(C_1-C_6)$alkylcarbamyls, N,N-di-$(C_1-C_6)$ alkylcarbamyls, thiocarbamyl, $(C_1-C_6)$ alkylsulphonyls, and Z groups;

$R_4$, $R_5$, $R_7$, $R_8$, $R'_4$, $R'_5$, $R'_7$ and $R'_8$, which may be identical or different, can be the point of attachment of a linker arm B, i.e, they can represent one of the two valencies of a linker arm B; otherwise they are chosen from a hydrogen atom; Z groups; $(C_1-C_6)$alkyls; $(C_1-C_6)$monohydroxyalkyls; $(C_2-C_6)$ polyhydroxyalkyls; $(C_1-C_6)$alkoxy$(C_1-C_6)$alkyls; aryls; benzyl; cyano$(C_1-C_6)$alkyls; carbamyl$(C_1-C_6)$ alkyls; N—$(C_1-C_6)$alkylcarbamyl$(C_1-C_6)$alkyls; N,N-di$(C_1-C_6)$alkylcarbamyl$(C_1-C_6)$alkyls; thiocarbamyl $(C_1-C_6)$alkyls; $(C_1-C_6)$trifluoroalkyls; $(C_1-C_6)$ sulphoalkyls;$(C_1-C_6)$alkylcarboxy$(C_1-C_6)$alkyls; $(C_1-C_6)$alkylsulphinyl$(C_1-C_6)$alkyls; $(C_1-C_6)$ aminosulphonylalkyls; $(C_1-C_6)$ N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; $(C_1-C_6)$ alkylcarbonyl$(C_1-C_6)$alkyls; $(C_1-C_6)$aminoalkyls; $(C_1-C_6)$aminoalkyls in which the amine is substituted with one or two identical or different radicals chosen from $(C_1-C_6)$alkyls, $(C_1-C_6)$ monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$ alkylcarbamyls, $(C_1-C_6)$alkylsulphonyls, formyls, trifluoro$(C_1-C_6)$-alkylcarbonyls, $(C_1-C_6)$ alkylcarboxyls, thiocarbamyl, and Z groups;

Z is chosen from unsaturated cationic groups of formulae (II) and (III) below, and saturated cationic groups of formula (IV) below:

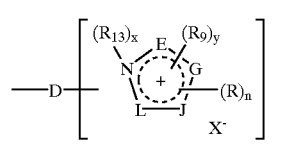
(II)

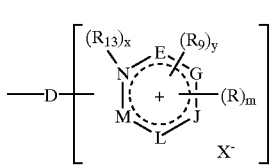
(III)

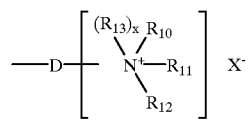
(IV)

in which:

D is a linker arm chosen from linear and branched alkyl chains, which are optionally interrupted by at least one hetero atom such as oxygen, sulphur and nitrogen, and which can optionally be substituted with at least one radical chosen from hydroxyls and $(C_1-C_6)$alkoxys, and which also can optionally bear at least one ketone function; in an embodiment of the invention, the alky chains comprise from 1 to 14 carbon atoms.

the ring members E, G, J, L and M, which may be identical or different, are chosen from carbon, oxygen, sulphur and nitrogen atoms;

n is chosen from the integers 0, 1, 2, 3, and 4;

m is chosen from the integers 0, 1, 2, 3, 4, and 5;

the radicals R, which may be identical or different, can be the point of attachment of a linker arm B, i.e., they can represent one of the two valencies of a linker arm B; otherwise they are chosen from a second group Z which is identical to or different from the first group Z, halogen atoms, a hydroxyl group, $(C_1-C_6)$alkyls, $(C_1-C_6)$monohydroxyalkyls, $(C_2-C_6)$ polyhydroxyalkyls, nitro, cyano, cyano$(C_1-C_6)$ alkyls, $(C_1-C_6)$alkoxyls, tri$(C_1-C_6)$alkylsilane $(C_1-C_6)$alkyls, amido, aldehydo, carboxyl, $(C_1-C_6)$ alkylcarbonyls, thio, $(C_1-C_6)$thioalkyls, $(C_1-C_6)$ alkylthios, amino, aminos protected with a radical chosen from $(C_1-C_6)$alkylcarbonyls, carbamyl, and $(C_1-C_6)$alkylsulphonyls; NHR" and NR"R'" groups in which R" and R'", which may be identical or different, are chosen from $(C_1-C_6)$alkyl radicals, $(C_1-C_6)$monohydroxyalkyl radicals and $(C_2-C_6)$ polyhydroxyalkyl radicals;

$R_9$ can be the point of attachment of a linker arm B, i.e., it can represent one of the two valencies of a linker arm B; otherwise $R_9$ is a radical chosen from $(C_1-C_6)$ alkyls, $(C_1-C_6)$monohydroxyalkyls, $(C_2-C_6)$polyhydroxyalkyls, cyano$(C_1-C_6)$alkyls, tri$(C_1-C_6)$alkylsilane$(C_1-C_6)$alkyls, $(C_1-C_6)$alkoxy$(C_1-C_6)$alkyls, carbamyl-$(C_1-C_6)$alkyls, $(C_1-C_6)$alkylcarboxy$(C_1-C_6)$-alkyls, benzyl, and a second group Z which is identical to or different from the first group Z;

$R_{10}$, $R_{11}$ and $R_{12}$, which may be identical or different, can be the point of attachment of a linker arm B, i.e., it can represent one of the two valencies of a linker arm B; otherwise they are radicals chosen from $(C_1-C_6)$alkyls, $(C_1-C_6)$monohydroxyalkyls, $(C_2-C_6)$polyhydroxyalkyls, $(C_1-C_6)$alkoxy$(C_1-C_6)$ alkyls, cyano$(C_1-C_6)$alkyls, aryls, benzyl, $(C_1-C_6)$ amidoalkyls, tri$(C_1-C_6)$alkylsilane$(C_1-C_6)$alkyls, and $(C_1-C_6)$aminoalkyls in which the amine is protected with a radical chosen from $(C_1-C_6)$ alkylcarbonyls, carbamyl, and $(C_1-C_6)$ alkylsulphonyls; two of the radicals $R_{10}$, $R_{11}$ and $R_{12}$ can together also form, with the nitrogen atom to which they are attached, a saturated 5- or 6-membered ring or a ring containing at least one additional hetero atom such as, for example, a pyrrolidine ring, a piperidine ring, a piperazine ring or a morpholine ring, it being possible for the ring to be unsubstituted or to be substituted with a substituent chosen from halogen atoms, a hydroxyl group, ($C_1$–$C_6$)alkyls, ($C_1$–$C_6$) monohydroxyalkyls, ($C_2$–$C_6$) polyhydroxyalkyls, nitro, cyano, cyano ($C_1$–$C_6$)alkyls, ($C_1$–$C_6$)alkoxys, tri($C_1$–$C_6$)alkylsilane($C_1$–$C_6$)alkyls, amido, aldehydo, carboxyl, keto($C_1$–$C_6$)alkyls, thio, ($C_1$–$C_6$) thioalkyls, ($C_1$–$C_6$)alkylthios, amino, and aminos protected with a radical chosen from ($C_1$–$C_6$) alkylcarbonyls, carbamyls, and ($C_1$–$C_6$) alkylsulphonyls;

one of the radicals $R_{10}$, $R_1$, and $R_{12}$ can also be chosen from a second group Z which is identical to or different from the first group Z;

$R_{13}$ can be the point of attachment of a linker arm B, i.e., it can represent one of the two valencies of a linker arm B; otherwise $R_{13}$ is a radical chosen from ($C_1$–$C_6$)alkyls; ($C_1$–$C_6$) monohydroxyalkyls; ($C_2$–$C_6$)polyhydroxyalkyls; aryls: benzyl; ($C_1$–$C_6$) aminoalkyls, ($C_1$–$C_6$)aminoalkyls in which the amine is protected with a radical chosen from ($C_1$–$C_6$)alkylcarbonyls, carbamyl, and ($C_1$–$C_8$) alkylsulphonyls; carboxy($C_1$–$C_6$)alkyls; cyano ($C_1$–$C_6$)alkyls; carbamyl($C_1$–$C_6$)alkyls; ($C_1$–$C_6$) trifluoroalkyls; tri($C_1$–$C_6$)alkylsilane-($C_1$–$C_6$)alkyl radical; a $C_1$–$C_6$ sulphonamidoalkyl radical; a ($C_1$–$C_6$)alkylcarboxy($C_1$–$C_6$)alkyls; ($C_1$–$C_6$) alkylsulphinyl($C_1$–$C_6$)alkyls; ($C_1$–$C_6$) alkylsulphonyl($C_1$–$C_6$)alkyls; ($C_1$–$C_6$)alkylketo ($C_1$–$C_6$)alkyls; N—($C_1$–$C_6$)alkylcarbamyl($C_1$–$C_6$) alkyls; N—($C_1$–$C_6$)alkylsulphonamido($C_1$–$C_6$) alkyls;

x and y are chosen from the integers 0 and 1; with the proviso that:

in the unsaturated cationic groups of formula (II):
when x=0, the linker arm D is attached to the nitrogen atom,
when x=1, the linker arm D is attached to one of the ring members E, G, J and L,
y can take the value 1 only:
1) when the ring members E, G, J and L simultaneously represent a carbon atom and when the radical $R_9$ is borne by the nitrogen atom of the unsaturated ring; or alternatively
2) when at least one of the ring members E, G, J and L represents a nitrogen atom to which the radical $R_9$ is attached;

in the unsaturated cationic groups of formula (III):
when x=0, the linker arm D is attached to the nitrogen atom,
when x=1, the linker arm D is attached to one of the ring members E, G, J, L and M,
y can take the value 1 only when at least one of the ring members E, G, J, L and M is chosen from divalent atoms and when the radical $R_9$ is borne by the nitrogen atom of the unsaturated ring;

in the cationic groups of formula (IV):
when x=0, then the linker arm D is attached to the nitrogen atom bearing the radicals $R_{10}$ to $R_{12}$,
when x=1, then two of the radicals $R_{10}$ to $R_{12}$ form, together with the nitrogen atom to which they are attached, a saturated 5- or 6-membered ring as defined above, and the linker arm D is borne by a carbon atom of the saturated ring;

$X^-$ is chosen from monovalent and divalent anions; in an embodiment of the invention, X− is chosen from halogen atoms such as chlorine, bromine, fluorine, and iodine, a hydroxide, a hydrogenosulphate, and ($C_1$–$C_6$)alkyl sulphates such as, for example, a methyl sulphate or an ethyl sulphate;

it being understood that:
the number of cationic groups Z is at least equal to 1;
when at least one of $R_4$, $R_5$, $R'_4$, $R'_5$, $R_7$, $R_8$, $R'_7$, and $R'_8$ is chosen from Z groups in which the linker arm D is chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$;
when at least one of $R_4$, $R_5$, $R'_4$, $R'_5$, $R_7$, $R_8$, $R'_7$, and $R'_8$ is the point of a attach of a linker arm B chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$.

As mentioned above, the colorations which can be obtained with the oxidation dye composition in accordance with the invention can be strong and can produce a wide range of shades and colours. They moreover can have excellent properties of resistance to the action of various external agents (e.g., light, bad weather, washing, permanent-waving, perspiration, friction). These properties can be particularly noteworthy as regards the resistance of the colorations obtained to the action of light, washing, permanent-waving and perspiration.

In formula (I) above, the alkyl and alkoxy radicals can be linear or branched.

Representative rings of the unsaturated groups Z of formula (II) above, include, for example, pyrrole, imidazole, pyrazole, oxazole, thiazole and triazole rings.

Representative rings of the unsaturated groups Z of formula (III) above, include, for example, pyridine, pyrimidine, pyrazine, oxazine and triazine rings.

Compounds of formula (I) above, include, for example:
1,3-bis{3-{3-[(2-aminoanilino)-N-propyl]}-3H-imidazol-1-ium}propane dibromide,
$N_1$,$N_3$-bis[3-N-(2-aminoanilino)propyl]-1,1,3,3-tetramethyldiammonium 1,3-propane dibromide,
1,4-bis{3-{2-[(2-aminoanilino)-N-ethyl]}-3H-imidazol-1-ium}butane dichloride,
1-[2-(2-aminoanilino)ethyl]-3-[-(2-aminoanilino)-propyl]-3H-imidazol-1-ium monochloride, and the acid addition salts thereof.

The compounds of formula (I) in accordance with the invention can be obtained according to methods which are known in the art, for example by reduction of the corresponding cationic nitro compounds (cationic "double" ortho-nitroanilines).

This reduction step (production of a primary aromatic amine), which may or may not be followed by a salification, is generally, for convenience, the final step of the synthesis.

This reduction can take place earlier in the sequence of reactions leading to the preparation of the compounds of formula (I), however, the primary amine created (for example by an acetylation, benzenesulphonation, etc. step), should be "protected," for example by known methods, before carrying out the desired substitution(s) or modification(s) (including quaternization) and then the amine function may in the end be "deprotected" (generally in acidic medium).

When the synthesis is complete, the compounds of formula (I) in accordance with the invention can, if necessary, be recovered by methods which are well known in the state of the art, such as crystallization or distillation.

Another subject of the invention is the use of the compounds of formula (I) and acid addition salts thereof in accordance with the invention as oxidation bases, coupling bases, or even as auto-oxidizing dyes for the oxidation dyeing of keratin fibres, and in of particular human keratin fibres such as the hair.

In an embodiment of the invention, the compounds of formula (I) and acid addition salts thereof are used as couplers for the oxidation dyeing of keratin fibres.

The invention also relates to a composition for the oxidation dyeing of keratin fibres, and in particular of human keratin fibres such as the hair, comprising, in a medium which is suitable for dyeing, at least one ingredient selected from compounds of formula (I) and acid addition salts thereof in accordance with the invention.

In an embodiment of the invention, the at least one ingredient is present in the composition in an amount ranging from 0.0005 to 12% by weight relative to the total weight of the dye composition, particularly the amount ranges from 0.005 to 6% by weight relative to this weight.

According to an embodiment of the invention, the dye composition also includes at least one oxidation base which can be chosen from the oxidation bases conventionally used in oxidation dyeing, including para-phenylenediamines, bis(phenylo)alkylenediamines, para-aminophenols, ortho-aminophenols and heterocyclic bases.

Representative para-phenylenediamines include, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, -(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, -(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

More particularly, the para-phenylenediamines mentioned above can be para-phenylenediamine, para-tolylenediamine, 2-isopropyl-para-phenylenediamine, 2-β-hydroxyethyl-para-phenylenediamine, 2β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Representative bis(phenyl)alkylenediamines include, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-(aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3-methylphenyl)ethylenediamine and 1,8-bis(2,5-diaminophenoxy)-3,5-dioxaoctane, and the acid addition salts thereof.

Representative para-aminophenols include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Representative ortho-aminophenols include, for example, 2-aminophenol, 2-amino-5-methylphenol, 2-amino-6-methylphenol and 5-acetamido-2-aminophenol, and the acid addition salts thereof.

Heterocyclic bases include, for example, pyridine derivatives, pyrimidine derivatives and pyrazole derivatives.

When they are used, these oxidation bases are present in the dye composition, in one embodiment, in an amount generally ranging from 0.0005 to 12% by weight relative to the total weight of the dye composition, particularly in an amount ranging from 0.005 to 6% by weight relative to this weight.

In addition to the compound(s) of formula (I) and acid addition salts thereof above, the dye composition in accordance with the invention can also include at least one additional coupler which can be chosen from couplers used conventionally in oxidation dyeing, including meta-phenylenediamines, meta-aminophenols, meta-diphenols and heterocyclic couplers such as, for example, indole derivatives, indolene derivatives, pyridine derivatives and pyrazolones, and the acid addition salts thereof.

Specific examples of suitable couplers include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the acid addition salts thereof.

When they are present, these couplers are present in the dye composition, in an embodiment of the invention, in an amount generally ranging from 0.0001 to 10% by weight relative to the total weight of the dye composition, and particularly the amount ranges from 0.005 to 5% by weight relative to this weight.

In general, the addition salts with an acid which can be used in the context of the dye compositions of the invention (compounds of formula (I), additional oxidation bases and couplers) are chosen from hydrochlorides, hydrobromides, sulphates, citrates, succinates, tartrates, lactates and acetates.

The medium which is suitable for dyeing (or the support) generally is chosen from water and a mixture of water and at least one organic solvent to dissolve the compounds which would not be sufficiently soluble in water. Suitable organic solvents include, for example, ($C_1$–$C_4$) lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol and phenoxyethanol, similar products and mixtures thereof.

The solvents can be present in an amount generally ranging from 1 to 40% by weight relative to the total weight of the dye composition, particularly in an amount ranging from 5 to 30% by weight.

In an embodiment of the invention, the pH of the dye composition generally ranges from 3 to 12, particularly from 5 to 11. The pH can be adjusted to the desired value using acidifying or basifying agents commonly used to dye keratin fibres.

Suitable acidifying agents include, for example, inorganic and organic acids such as hydrochloric acid, orthophosphoric acid, sulphuric acid, carboxylic acids such as acetic acid, tartaric acid, citric acid and lactic acid, and sulphonic acids.

Suitable basifying agents include, for example, aqueous ammonia, alkaline carbonates, alkanolamines such as mono-, di- and triethanolamine and derivatives thereof, sodium hydroxide, potassium hydroxide and the compounds of formula (V) below:

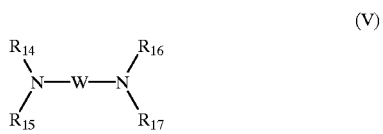

in which W is chosen from propylene residues optionally substituted with a radical chosen from hydroxyl and $(C_1-C_6)$ alkyls; $R_{14}$, $R_{15}$, $R_{16}$ and $R_{17}$, which may be identical or different, are chosen from a hydrogen atom, $(C_1-C_8)$alkyl radicals and $(C_1-C_6)$ hydroxyalkyl radicals.

The oxidation dye compositions in accordance with the invention can also include at least one direct dye, in particular to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres for a period which is sufficient to develop the desired coloration, either in air or using an oxidizing agent. The dye composition can optionally contain oxidation catalysts, in order to accelerate the oxidation process.

According to an embodiment of the process of the invention, the coloration of the fibres can be carried out without addition of an oxidizing agent, merely by contact with atmospheric oxygen, i.e., the air.

According to another embodiment of the process of the invention, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner.

According to this embodiment of the dyeing process of the invention, the dye composition described above can be mixed, at the time of use, with an oxidizing composition containing, in a medium which is suitable for dyeing, at least one oxidizing agent present in an amount which is sufficient to develop a coloration. The mixture obtained is then applied to the keratin fibres and left in place for an amount of time sufficient to develop the desired coloration, after which the fibres are rinsed, washed with shampoo, rinsed again and dried. In an embodiment of the invention, the time period for developing the desired coloration is generally 3 to 50 minutes, and can be 5 to 30 minutes.

The oxidizing agent present in the oxidizing composition and as defined above can be chosen from the oxidizing agents conventionally used for the oxidation dyeing of keratin fibres, including hydrogen peroxide, urea peroxide, alkali metal bromates and persalts such as perborates and persulphates, and enzymes such as peroxidases and 2-electron oxidoreductases. In an embodiment of the invention, hydrogen peroxide is the oxidizing agent.

In one embodiment of the invention, the pH of the oxidizing composition containing the oxidizing agent as defined above is such that, after mixing with the dye composition, the pH of the resultant composition applied to the keratin fibres generally ranges from 3 to 12, particularly from 5 to 11. The pH is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or kit or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913, the disclosure of which is herein specifically incorporated by reference.

The examples which follow are intended to illustrate the invention without, however, limiting its scope.

PREPARATION EXAMPLES

Preparation Example 1

Synthesis of 1,3-bis-1-{3-{3-[(2-aminoanilino)-N-propyl]}-3H-imidazol-1-ium}propane Dibromide Dihydrobromide

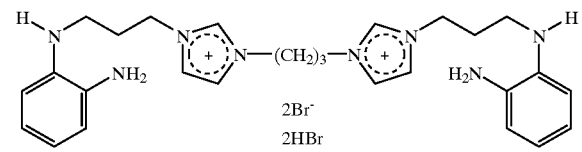

a) Synthesis of (3-imidazol-1-ylpropyl)(2-nitrophenyl)amine

A mixture of 187.8 g (1.5 mol) of 3-imidazol-1-ylpropylamine and 82.8 g (0.6 mol) of potassium carbonate in 280 ml of water was heated on a boiling water bath.

141.1 g (1 mol) of 1-fluoro-2-nitrobenzene was added dropwise over 50 minutes and maintained at a temperature of 90–95° C. for 2 hours.

The mixture was cooled in a bath of ice and the crystallized precipitate was filtered off, washed with water and recrystallized from refluxing isopropanol.

109.3 g of orange-yellow crystals melting at 80° C. (Kofler) were obtained, the elemental analysis for which product, calculated for $C_{12}H_{14}N_4O_2$, was:

| | % | | | |
|---|---|---|---|---|
| | C | H | N | O |
| Calculated | 58.53 | 5.73 | 22.75 | 12.99 |
| Found | 58.40 | 5.78 | 22.54 | 13.07 | b) Quaternization of (3-imidazol-1-ylpropyl)(2-nitrophenyl)amine

A mixture of 74.0 g (0.3 mol) of 3-imidazol-1-ylpropyl)(2-nitrophenyl)amine obtained above in the preceding step and 30.3 g (0.15 mol) of 1,3-dibromopropane in 250 ml of isobutanol was heated for 11 hours at 120° C. A gum in suspension crystallized.

The mixture was cooled and the crystallized precipitate was filtered off, re-impasted twice in the minimum amount of absolute ethanol and recrystallized from refluxing absolute ethanol.

86.4 g of orange crystals melting at 166° C. (Kofler) were obtained, the elemental analysis for which product, calculated for $C_{27}H_{34}N_8O_4Br_2$, was:

| | % | | | | |
|---|---|---|---|---|---|
| | C | H | N | O | Br |
| Calculated | 46.70 | 4.94 | 16.14 | 9.22 | 23.01 |
| Found | 46.59 | 5.00 | 16.15 | 9.41 | 22.97 | c) Reduction 52.0 g (0.075 mol) of the compound obtained above in the preceding step, 12 g of 5% palladium on charcoal (containing 50% water), 300 ml of 960 ethanol and 300 ml of water were placed in a hydrogenator.

The reduction took place in half an hour at a hydrogen pressure of about 8 bar and at a temperature which was gradually raised to 75° C.

After filtration of the catalyst under nitrogen, the mixture was poured into 50 ml of 48% hydrobromic acid and the filtrate was evaporated to dryness under reduced pressure.

The crystalline compound obtained was taken up in absolute ethanol, filtered off, recrystallized from a mixture of refluxing ethanol/water and dried at 40° C. under vacuum and over potassium hydroxide.

29.3 g of pink-white crystals of 1,3-bis-1-{3-{3-[(2-aminoanilino)-N-propyl]}-3H-imidazol-1-ium}propane dibromide dihydrobromide melting at 190–192° C. (Kofler) were obtained, the elemental analysis of which product, calculated for $C_{27}H_{40}N_8Br_4$, was:

| | % | | | |
|---|---|---|---|---|
| | C | H | N | Br |
| Calculated | 40.73 | 5.06 | 14.07 | 40.14 |
| Found | 40.41 | 5.10 | 13.77 | 40.21 |

Preparation Example 2

Preparation of $N_1,N_3$-bis[3-N-(2-aminoanilino)propyl]-1,1,3,3-tetramethyldiammonium 1,3-propane Dibromide Dihydrobromide

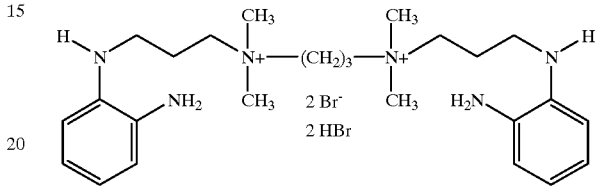

a) Quaternization of N,N-dimethyl-N'-(2-nitrophenyl)-ethane-1,2-diamine

The procedure described above for Example 1, step b) was used.

Starting with 62.7 g (0.3 mol) of N,N-dimethyl-N'-(2-nitrophenyl)ethane-1,2-diamine and 30.3 g (0.15 mol) of 1,3-dibromopropane, and after recrystallization from a refluxing ethanol/water mixture, 67.0 g of orange crystals melting at 220° C. (Kofler) were obtained, the elemental analysis of which product, calculated for $C_{23}H_{36}N_6O_4Br_2 + H_2O$, was:

| | % | | | | |
|---|---|---|---|---|---|
| | C | H | N | O | Br |
| Calculated | 43.27 | 6.00 | 13.16 | 12.53 | 25.03 |
| Found | 43.44 | 6.14 | 12.59 | 12.72 | 24.74 | b) Reduction

The procedure described above for Example 1, step c) was used.

Starting with 46.5 g (0.728 mol) of the compound prepared above in the preceding step, and after reduction, salification with hydrobromic acid and recrystallization from a refluxing ethanol/water mixture, 24.4 g of pink-white crystals of $N_1,N_3$-bis[3-N-(2-aminoanilino)propyl]-1,1,3,3-tetramethyldiammonium 1,3-propane dihydrobromide melting at more than 260° C. (Kofler) were obtained, the elemental analysis of which product, calculated for $C_{23}H_{42}N_6Br_4$, was:

| | % | | | |
|---|---|---|---|---|
| | C | H | N | Br |
| Calculated | 38.25 | 5.86 | 11.64 | 44.25 |
| Found | 38.25 | 5.91 | 11.44 | 43.86 |

APPLICATION EXAMPLES

Examples 1 to 8 of Dyeing in Alkaline Medium

The dye compositions below in accordance with the invention were prepared (contents in grams):

| EXAMPLE | 1 | 2 | 3 | 4 | 5 | 6 | 7 | 8 |
|---|---|---|---|---|---|---|---|---|
| 1,3-bis-1-{3-{3-[(2-Aminoanilino)-N-propyl]}-3H-imidazol-1-ium}propane dibromide dihydrobromide (compound of formula (I)) | 2.388 | — | — | 2.388 | 2.388 | 2.388 | — | — |
| $N_1,N_3$-bis[3-N-(2-Aminoanilino)propyl]-1,1,3,3-tetramethyldiammonium 1,3-propane dibromide dihydrobromide (compound of formula (I)) | — | 2.166 | 2.166 | — | — | — | 2.166 | 2.166 |
| 3,7-Diaminopyrazolopyrimidine dihydrochloride (oxidation base) | 0.666 | — | — | — | — | — | — | — |
| 4-Hydroxyindole (coupler) | — | 0.399 | — | — | — | — | — | — |
| 1,3-Dihydroxybenzene (coupler) | — | — | 0.33 | — | 0.33 | — | — | — |
| 2,4-Diaminophenoxyethanol dihydrochloride (coupler) | — | — | — | 0.723 | — | — | — | — |
| 4,5-Diamino-1-ethyl-3-methylpyrazole dihydrochloride (oxidation base) | — | — | — | — | — | 0.639 | — | — |
| meta-Aminophenol (coupler) | — | — | — | — | — | — | 0.327 | — |
| para-Tolylenediamine dihydrochloride (oxidation base) | — | — | — | — | — | — | — | 0.585 |
| Common dye support No. 1 | (*) | (*) | (*) | (*) | (*) | (*) | (*) | (*) |
| Demineralized water q.s.p. | 100 g | 100 g | 100 g | 100 g | 100 g | 100 g | 100 g | 100 g |

At the time of use, each of the above dye compositions was mixed, weight for weight, with a 20-volumes hydrogen peroxide solution (6% by weight) of pH 3.

The mixture obtained was applied to locks of permanent-waved grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 1 | 10 ± 0.2 | natural light chestnut |
| 2 | 10 ± 0.2 | matt warm golden blonde |
| 3 | 10 ± 0.2 | iridescent coppery golden light blonde |
| 4 | 10 ± 0.2 | dull green dark blonde |
| 5 | 10 ± 0.2 | dull golden coppery blonde |
| 6 | 10 ± 0.2 | matt coppery golden blonde |
| 7 | 10 ± 0.2 | golden very light blonde |
| 8 | 10 ± 0.2 | ash natural blonde |

At the time of use, each of the above dye compositions was mixed, weight for weight, with a 20-volumes hydrogen peroxide solution (6% by weight) of pH 3.

The mixture obtained was applied to locks of permanent-waved grey hair containing 90% white hairs, for 30 minutes. The locks were then rinsed, washed with a standard shampoo, rinsed again and then dried.

the shades obtained are given in the table below:

| EXAMPLE | dyeing pH | shade obtained |
|---|---|---|
| 9 | 5.7 ± 0.2 | matt golden ash light blonde |
| 10 | 5.7 ± 0.2 | golden natural blonde |
| 11 | 5.7 ± 0.2 | coppery golden blonde |
| 12 | 5.7 ± 0.2 | coppery golden light blonde |
| 13 | 5.7 ± 0.2 | matt ash golden light blonde |
| 14 | 5.7 ± 0.2 | ash chestnut |
| 15 | 5.7 ± 0.2 | coppery golden blonde |
| 16 | 5.7 ± 0.2 | natural light chestnut |

Examples 9 to 16 of Dyeing in Neutral Medium

The dye compositions below in accordance with the invention were prepared (contents in grams):

Examples 17 to 24 of Dyeing in Alkaline Medium

The dye compositions below in accordance with the invention were prepared (contents in grams):

| EXAMPLE | 9 | 10 | 11 | 12 | 13 | 14 | 15 | 16 |
|---|---|---|---|---|---|---|---|---|
| 1,3-bis-1-{3-{3-[(2-Aminoanilino)-N-propyl]}-3H-imidazol-1-ium}propane dibromide dihydrobromide (compound of formula (I)) | — | 2.388 | 2.388 | — | — | 2.388 | 2.388 | — |
| $N_1,N_3$-bis[3-N-(2-Aminoanilino)propyl]-1,1,3,3-tetramethyldiammonium 1,3-propane dibromide dihydrobromide (compound of formula (I)) | 2.166 | — | — | 2.166 | 2.166 | — | — | 2.166 |
| 2,4-Diaminophenoxyethanol dihydrochloride (coupler) | 0.723 | — | — | — | — | — | — | — |
| 4-Hydroxyindole (coupler) | — | 0.399 | — | — | — | — | — | — |
| meta-Aminophenol (coupler) | — | — | 0.327 | — | — | — | — | — |
| 4,5-Diamino-1-ethyl-3-methylpyrazole dihydrochloride (oxidation base) | — | — | — | — | 0.639 | — | — | — |
| para-Tolylenediamine dihydrochloride (oxidation base) | — | — | — | — | — | 0.585 | — | — |
| 3,7-Diaminopyrazolopyrimidine dihydrochloride (oxidation base) | — | — | — | — | — | — | — | 0.666 |
| Common dye support No. 2 | () | () | () | () | () | () | () | () |
| Demineralized water q.s.p. | 100 g | 100 g | 100 g | 100 g | 100 g | 100 g | 100 g | 100 g |

| EXAMPLE | 17 | 18 | 19 | 20 | 21 | 22 | 23 | 24 |
|---|---|---|---|---|---|---|---|---|
| 1,3-bis-1-{3-{3-[(2-Aminoanilino)-N-propyl]}-3H-imidazol-1-ium}propane dibromide dihydrobromide (compound of formula (I)) | — | 2.388 | 2.388 | — | — | 2.388 | — | 2.388 |
| $N_1,N_3$-bis[3-N-(2-Aminoanilino)propyl]-1,1,3,3-tetramethyldiammonium 1,3-propane dibromide dihydrobromide (compound of formula (I)) | 2.166 | — | — | 2.166 | 2.166 | — | 2.166 | — |
| 4,5-Diamino-1-ethyl-3-methylpyrazole dihydrochloride (oxidation base) | 0.639 | — | — | — | — | — | — | — |
| meta-Aminophenol (coupler) | — | 0.327 | — | — | — | — | — | — |
| 4-Hydroxyindole (coupler) | — | — | 0.399 | — | — | — | — | — |
| 2,4-Diaminophenoxyethanol dihydrochloride (coupler) | — | — | — | 0.723 | — | — | — | — |
| para-Tolylenediamine dihydrochloride (oxidation base) | — | — | — | — | 0.585 | — | — | — |
| 3,7-Diaminopyrazolopyrimidine dihydrochloride (oxidation base) | — | — | — | — | — | — | 0.666 | — |
| Common dye support No. 1 | (*) | (*) | (*) | (*) | (*) | (*) | (*) | (*) |
| Demineralized water q.s.p. | 100 g | 100 g | 100 g | 100 g | 100 g | 100 g | 100 g | 100 g |

At the time of use, each of the above dye compositions was mixed, weight for weight, with an aqueous solution containing $6 \times 10^{-3}$ mol % of ammonium persulphate.

The mixture obtained was applied to locks of permanent-wave grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 17 | 10 ± 0.2 | matt golden blonde |
| 18 | 10 ± 0.2 | matt ash blonde |
| 19 | 10 ± 0.2 | matt golden ash light blonde |
| 20 | 10 ± 0.2 | matt ash blonde |
| 21 | 10 ± 0.2 | matt ash golden light blonde |
| 22 | 10 ± 0.2 | matt ash dark blond |
| 23 | 10 ± 0.2 | ash natural blonde |
| 24 | 10 ± 0.2 | iridescent golden natural blonde |

Examples 25 to 32 of Dyeing in Neutral Medium

The dye compositions below in accordance with the invention were prepared (contents in grams):

This identical to the one used for Examples 9 to 16 above.

At the time of use, each of the above dye compositions was mixed, weight for weight, with an aqueous solution containing $6 \times 10^{-3}$ mol % of ammonium persulphate.

mixture obtained was applied to locks of permanent-wave grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 25 | 5.7 ± 0.2 | iridescent golden very light blonde |
| 26 | 5.7 ± 0.2 | matt golden natural light blonde |
| 27 | 5.7 ± 0.2 | coppery golden light blonde |
| 28 | 5.7 ± 0.2 | golden ash natural blonde |
| 29 | 5.7 ± 0.2 | golden ash light blonde |
| 30 | 5.7 ± 0.2 | matt golden ash light blonde |
| 31 | 5.7 ± 0.2 | ash light blonde |
| 32 | 5.7 ± 0.2 | matt ash golden blonde |

| EXAMPLE | 25 | 26 | 27 | 28 | 29 | 30 | 31 | 32 |
|---|---|---|---|---|---|---|---|---|
| 1,3-bis-1-{3-{3-[(2-Aminoanilino)-N-propyl]}-3H-imidazol-1-ium}propane dibromide dihydrobromide (compound of formula (I)) | — | 2.388 | 2.388 | 2.388 | — | — | — | 2.388 |
| $N_1,N_3$-bis[3-N-(2-Aminoanilino)propyl]-1,1,3,3-tetramethyldiammonium 1,3-propane dibromide dihydrobromide (compound of formula (I)) | 2.166 | — | — | — | 2.166 | 2.166 | 2.166 | — |
| 1,3-Dihydroxybenzene (coupler) | 0.33 | — | 0.33 | — | — | — | — | — |
| 4,5-Diamino-1-ethyl-3-methylpyrazole dihydrochloride (oxidation base) | — | 0.639 | — | — | — | — | — | — |
| 2,4-Diaminophenoxyethanol dihydrochloride (coupler) | — | — | — | 0.723 | — | — | — | — |
| para-Tolylenediamine dihydrochloride (oxidation base) | — | — | — | — | 0.585 | — | — | — |
| meta-Aminophenol (coupler) | — | — | — | — | — | 0.327 | — | — |
| 4-Hydroxyindole (coupler) | — | — | — | — | — | — | 0.399 | — |
| 3,7-Diaminopyrazolopyrimidine dihydrochloride (oxidation base) | — | — | — | — | — | — | — | 0.666 |
| Common dye support No. 2 | () | () | () | () | () | () | () | () |
| Demineralized water q.s.p. | 100 g | 100 g | 100 g | 100 g | 100 g | 100 g | 100 g | 100 g |

Examples 33 and 34 of Dyeing in Air

At the time of use, the dye compositions below in accordance with the invention were prepared (contents in grams):

| EXAMPLE | 33 | 34 |
|---|---|---|
| 1,3-bis-1-{3-{3-[(2-Aminoanilino)-N-propyl]}-3H-imidazol-1-ium}propane dibromide dihydrobromide (compound of formula (I)) | 4.776 | — |
| $N_1,N_3$-bis[3-N-(2-Aminoanilino)propyl]-1,1,3,3-tetramethyldiammonium 1,3-propane dibromide dihydrobromide (compound of formula (I)) | — | 4.332 |
| 96° Ethanol | 20 | 20 |
| pH 9.5 $NH_4OH/NH_4Cl$ (1M/1M) buffer | 10 | 10 |
| Demineralized water qs | 100 g | 100 g |

These compositions were applied to locks of permanent-waved grey hair containing 90% white hair, and the coloration was allowed to develop for 30 minutes, without addition of any oxidizing agent other than atmospheric oxygen.

The hair was then rinsed, washed with a standard shampoo, rinsed again and then dried.

The hair was dyed in the shade given in the table below:

| EXAMPLE | SHADE OBTAINED |
|---|---|
| 33 | Strong golden copper |
| 34 | Golden copper |

What is claimed is:

1. A compound of formula (I) below, or an acid addition salt thereof:

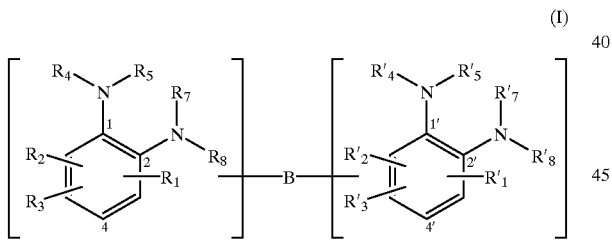

(I)

in which:

B is a linker arm chosen from linear and branched alkyl chains, which can be optionally interrupted with at least one group chosen from Z groups and hetero atoms, and which can be optionally substituted with at least one substituent chosen from hydroxyls and ($C_1$–$C_6$) alkoxys, and which can optionally bear at least one ketone function;

$R_1$, $R_2$, $R_3$, $R'_1$, $R'_2$ and $R'_3$, which may be identical or different, can be the point of attachment of a linker arm B, otherwise, they are chosen from a hydrogen atom; halogens; Z groups; ($C_1$–$C_6$)alkylcarbonyls; amino ($C_1$–$C_6$)alkylcarbonyls; N—Z-amino($C_1$–$C_6$) alkylcarbonyls; N—($C_1$–$C_6$)alkylamino($C_1$–$C_6$) alkylcarbonyls; N,N-di($C_1$–$C_6$)alkylamino($C_1$–$C_6$) alkylcarbonyls; amino($C_1$–$C_6$)alkylcarbonyl($C_1$–$C_6$) alkyls; N—Z-amino($C_1$–$C_6$)alkylcarbonyl($C_1$–$C_6$) alkyls; N—($C_1$–$C_6$)alkylamino($C_1$–$C_6$)alkylcarbonyl ($C_1$–$C_6$)alkyls; N,N-di($C_1$–$C_6$)alkylamino($C_1$–$C_6$) alkylcarbonyl($C_1$–$C_6$)alkyls; carboxyl;($C_1$–$C_6$) alkylcarboxyls; ($C_1$–$C_6$)alkylsulphonyls; aminosulphonyls; N—Z-aminosulphonyls; ($C_1$–$C_6$)N-alkylaminosulphonyls; N,N-di($C_1$–$C_6$) alkylaminosulphonyls; ($C_1$–$C_6$)aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; carbamyl; N—($C_1$–$C_6$)alkylcarbamyls; N,N-di($C_1$–$C_6$) alkylcarbamyls; carbamyl($C_1$–$C_6$)alkyls; N—($C_1$–$C_6$) alkylcarbamyl($C_1$–$C_6$)alkyls; N,N-di($C_1$–$C_6$) alkylcarbamyl($C_1$–$C_6$)alkyls; ($C_1$–$C_6$)alkyls; ($C_1$–$C_6$) monohydroxyalkyls; ($C_2$–$C_6$)polyhydroxyalkyls; ($C_1$–$C_6$)alkoxy($C_1$–$C_6$)alkyls; ($C_1$–$C_6$)trifluoroalkyls; cyano; $OR_6$ and $SR_6$ groups; amino groups protected with a radical chosen from ($C_1$–$C_6$)alkylcarbonyls, ($C_1$–$C_6$)alkylcarboxyls, trifluoro($C_1$–$C_6$) alkylcarbonyls, amino($C_1$–$C_6$)alkylcarbonyls, N—Z-amino($C_1$–$C_6$)alkylcarbonyls, N—($C_1$–$C_6$)alkylamino ($C_1$–$C_6$)alkylcarbonyls, N,N-di($C_1$–$C_6$)alkylamino ($C_1$–$C_6$)alkylcarbonyls, ($C_1$–$C_6$)alkylcarboxyls, carbamyl, N—($C_1$–$C_6$)alkylcarbamyls, N,N-di($C_1$–$C_6$) alkylcarbamyls, ($C_1$–$C_6$)alkylsulphonyls, aminosulphonyls, N—Z-aminosulphonyls, ($C_1$–$C_6$)N-alkylaminosulphonyl, N,N-di($C_1$–$C_6$) alkylaminosulphonyls, thiocarbamyl, formyl, and Z groups in which the linker arm B comprises a ketone function directly attached to the nitrogen atom of the amino group;

$R_6$ can be the point of attachment of a linker arm B, otherwise $R_6$ is a radical chosen from ($C_1$–$C_6$)alkyls; ($C_1$–$C_6$)monohydroxyalkyls; ($C_2$–$C_6$) polyhydroxyalkyls; Z groups; ($C_1$–$C_6$)alkoxy($C_1$–$C_6$) alkyls; aryls; benzyl; carboxy($C_1$–$C_6$)alkyls; ($C_1$–$C_6$) alkylcarboxy($C_1$–$C_6$)alkyls; cyano($C_1$–$C_6$)alkyls; carbamyl($C_1$–$C_6$)alkyls; N—($C_1$–$C_6$)alkylcarbamyl ($C_1$–$C_6$)alkyls; N,N-di($C_1$–$C_6$)alkylcarbamyl($C_1$–$C_6$) alkyls; ($C_1$–$C_6$)trifluoroalkyls; ($C_1$–$C_6$) aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; ($C_1$–$C_6$) alkylsulphinyl-($C_1$–$C_6$)alkyls;($C_1$–$C_6$)alkylsulphonyl-($C_1$–$C_6$)alkyls;($C_1$–$C_6$)alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$) monohydroxyalkyls, ($C_2$–$C_6$)polyhydroxyalkyls, ($C_1$–$C_6$)alkylcarbonyls, formyl, trifluoro-($C_1$–$C_6$) alkylcarbonyls, ($C_1$–$C_6$)alkylcarboxyls, carbamyl, N—($C_1$–$C_6$)alkylcarbamyls, N,N-di-($C_1$–$C_6$) alkylcarbamyls, thiocarbamyl, ($C_1$–$C_6$) alkylsulphonyls, and Z groups; $R_4$, $R_5$, $R_7$, $R_8$, $R'_4$, $R'_5$, $R'_7$ and $R'_8$, which may be identical or different, can be the point of attachment of a linker arm B, otherwise they are chosen from a hydrogen atom; Z groups; ($C_1$–$C_6$)alkyls;($C_1$–$C_6$)monohydroxyalkyls; ($C_2$–$C_6$) polyhydroxyalkyls; ($C_1$–$C_6$)alkoxy($C_1$–$C_6$)alkyls; aryls; benzyl; cyano($C_1$–$C_6$)alkyls; carbamyl($C_1$–$C_6$) alkyls; N—($C_1$–$C_6$)alkylcarbamyl($C_1$–$C_6$)alkyls; N,N-di($C_1$–$C_6$)alkylcarbamyl($C_1$–$C_6$)alkyls; thiocarbamyl ($C_1$–$C_6$)alkyls; ($C_1$–$C_6$)trifluoroalkyls; ($C_1$–$C_6$) sulphoalkyls;($C_1$–$C_6$)alkylcarboxy($C_1$–$C_6$)alkyls; ($C_1$–$C_6$)alkylsulphinyl($C_1$–$C_6$)alkyls; ($C_1$–$C_6$) aminosulphonylalkyls; ($C_1$–$C_6$) N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; ($C_1$–$C_6$) alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from $(C_1-C_6)$alkyls, $(C_1-C_6)$ monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$alkylcarbamyls, $(C_1-C_6)$alkylsulphonyls, formyls, trifluoro$(C_1-C_6)$-alkylcarbonyls, $(C_1-C_6)$alkylcarboxyls, thiocarbamyl, and Z groups;

Z is chosen from unsaturated cationic groups of formulae (II) and (III) below, and saturated cationic groups of formula (IV) below:

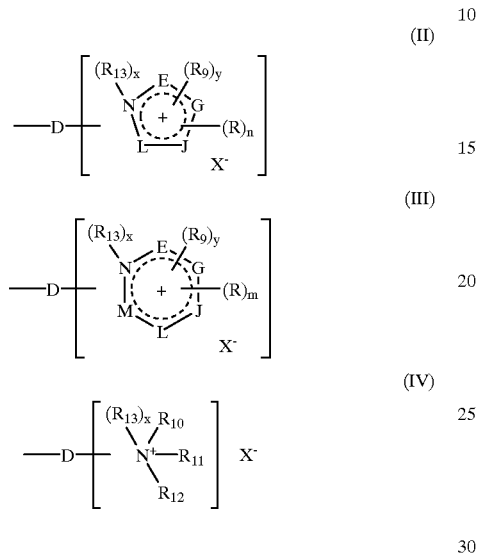

in which:

D is a linker arm chosen from linear and branched alkyl chains, which are optionally interrupted by at least one hetero atom, and which can optionally be substituted with at least one radical chosen from hydroxyls and $(C_1-C_6)$alkoxys, and which also can optionally bear at least one ketone function;

the ring members E, G, J, L and M, which may be identical or different, are chosen from carbon, oxygen, sulphur and nitrogen atoms;

n is chosen from the integers 0, 1, 2, 3, and 4;

m is chosen from the integers 0, 1, 2, 3, 4, and 5;

the radicals R, which may be identical or different, can be the point of attachment of a linker arm B, otherwise they are chosen from a second group Z which is identical to or different from the first group Z, halogen atoms, a hydroxyl group, $(C_1-C_6)$alkyls, $(C_1-C_6)$monohydroxyalkyls, $(C_2-C_6)$polyhydroxyalkyls, nitro, cyano, cyano$(C_1-C_6)$alkyls, $(C_1-C_6)$alkoxyls, tri$(C_1-C_6)$alkylsilane$(C_1-C_6)$alkyls, amidos, aldehydo, carboxyl, $(C_1-C_6)$alkylcarbonyls, thio, $(C_1-C_6)$thioalkyls, $(C_1-C_6)$alkylthios, amino, aminos protected with a radical chosen from $(C_1-C_6)$alkylcarbonyls, carbamyl, and $(C_1-C_6)$alkylsulphonyls; and NHR" and NR"R'" groups in which R" and R'", which may be identical or different, are chosen from $(C_1-C_6)$ alkyl radicals, $(C_1-C_6)$monohydroxyalkyl radicals and $(C_2-C_6)$ polyhydroxyalkyl radicals;

$R_9$ can be the point of attachment of a linker arm B, otherwise $R_9$ is a radical chosen from $(C_1-C_6)$alkyls, $(C_1-C_6)$monohydroxyalkyls, $(C_2-C_6)$ polyhydroxyalkyls, cyano$(C_1-C_6)$alkyls, tri$(C_1-C_6)$alkylsilane$(C_1-C_6)$alkyls, $(C_1-C_6)$alkoxy$(C_1-C_6)$alkyls, carbamyl-$(C_1-C_6)$alkyls, $(C_1-C_6)$alkylcarboxy$(C_1-C_6)$alkyls, benzyl, and a second group Z which is identical to or different from the first group Z;

$R_{10}$, $R_{11}$ and $R_{12}$, which may be identical or different, can be the point of attachment of a linker arm B, otherwise they are radicals chosen from $(C_1-C_6)$ alkyls, $(C_1-C_6)$monohydroxyalkyls, $(C_2-C_6)$ polyhydroxyalkyls, $(C_1-C_6)$alkoxy$(C_1-C_6)$alkyls, cyano$(C_1-C_6)$alkyls, aryls, benzyl, $(C_1-C_6)$ amidoalkyls, tri$(C_1-C_6)$alkylsilane$(C_1-C_6)$alkyls, and $(C_1-C_6)$aminoalkyls in which the amine is protected with a radical chosen from $(C_1-C_6)$ alkylcarbonyls, carbamyl, and $(C_1-C_6)$ alkylsulphonyls; two of the radicals $R_{10}$, $R_{11}$, and $R_{12}$ can together also form, with the nitrogen atom to which they are attached, a saturated 5- or 6-membered ring or a ring containing at least one additional hetero atom, it being possible for the ring to be unsubstituted or to be substituted with a substituent chosen from halogen atoms, a hydroxyl group, $(C_1-C_6)$ alkyls, $(C_1-C_6)$monohydroxyalkyls, $(C_2-C_6)$ polyhydroxyalkyls, nitro, cyano, cyano$(C_1-C_6)$ alkyls, $(C_1-C_6)$alkoxys, tri$(C_1-C_6)$alkylsilane $(C_1-C_6)$alkyls, amido, aldehydo, carboxyl, keto $(C_1-C_6)$alkyls, thio, $(C_1-C_6)$thioalkyls, $(C_1-C_6)$ alkylthios, amino, and aminos protected with a radical chosen from $(C_1-C_6)$alkylcarbonyls, carbamyl, and $(C_1-C_6)$alkylsulphonyls; one of the radicals $R_{10}$, $R_{11}$ and $R_{12}$ can also be chosen from a second group Z which is identical to or different from the first group Z;

$R_{13}$ can be the point of attachment of a linker arm B, otherwise $R_{13}$ is a radical chosen from $(C_1-C_6)$ alkyls; $(C_1-C_6)$monohydroxy-alkyls; $(C_2-C_6)$ polyhydroxyalkyls; aryls; benzyl; $(C_1-C_6)$aminoalkyls, $(C_1-C_6)$aminoalkyls in which the amine is protected with a radical chosen from $(C_1-C_6)$alkylcarbonyls, carbamyl, and $(C_1-C_6)$alkylsulphonyls; carboxy $(C_1-C_6)$alkyls; cyano$(C_1-C_6)$alkyls; carbamyl $(C_1-C_6)$alkyls; $(C_1-C_6)$trifluoroalkyls; tri$(C_1-C_6)$ alkylsilane-$(C_1-C_6)$alkyl radical; a $C_1-C_6$ sulphonamidoalkyl radical; a $(C_1-C_6)$alkylcarboxy $(C_1-C_6)$alkyls; $(C_1-C_6)$alkylsulphinyl$(C_1-C_6)$ alkyls; $(C_1-C_6)$alkylsulphonyl$(C_1-C_6)$alkyls; $(C_1-C_6)$alkylketo$(C_1-C_6)$alkyls; N—$(C_1-C_6)$ alkylcarbamyl$(C_1-C_6)$alkyls; N—$(C_1-C_6)$ alkylsulphonamido$(C_1-C_6)$alkyls;

x and y are chosen from the integers 0 and 1; with the proviso that:

in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_9$ is borne by the nitrogen atom of the unsaturated ring; or alternatively
2) when at least one of the ring members E, G, J and L represents a nitrogen atom to which the radical $R_9$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical $R_9$ is borne by the nitrogen atom of the unsaturated ring;

in the cationic groups of formula (IV):
when x=0, then the linker arm D is attached to the nitrogen atom bearing the radicals $R_{10}$ to $R_{12}$,
when x=1, then two of the radicals $R_{10}$ to $R_{12}$ form, together with the nitrogen atom to which they are attached, a saturated 5- or 6-membered ring as defined above, and the linker arm D is borne by a carbon atom of the saturated ring;

$X^-$ is chosen from monovalent and divalent anions; it being understood that:
the number of cationic groups Z is at least equal to 1;
when at least one of $R_4$, $R_5$, $R'_4$, $R'_5$, $R_7$, $R_8$, $R'_7$, and $R'_8$ is chosen from Z groups in which the linker arm D is chosen from alkyl chains comprising a ketone function, then the ketone function is not directly attached to the nitrogen atom of the group $-NR_4R_5$, $-NR'_4R'_5$, $-NR_7R_8$ or $-NR'_7R'_8$;
when at least one of $R_4$, $R_5$, $R'_4$, $R'_5$, $R_7$, $R_8$, $R'_7$, and $R'_8$ is the point of a attachment of linker arm B chosen from alkyl chains comprising a ketone function, then the ketone function is not directly attached to the nitrogen atom of the group $-NR_4R_5$, $-NR'_4R'_5$, $-NR_7R_8$ or $-NR'_7R'_8$.

2. The compound or acid addition salt of claim 1, wherein the alkyl chains of said B linker arm and of said D linker arm comprise from 1 to 14 carbon atoms; the heteroatoms optionally interrupting the alkyl chains of said B linker arm and said D linker arm are chosen from oxygen, sulfur and nitrogen; and wherein the ring containing at least one additional heteroatom and which is formed from two of $R_{10}$, $R_{11}$, and $R_{12}$ is chosen from pyrrolidine, piperidine, piperazine, and morpholine.

3. The compound or acid addition salt of claim 1, wherein the rings in the unsaturated groups Z of formula (II) are chosen from pyrrole, imidazole, pyrazole, oxazole, thiazole and triazole rings.

4. The compound or acid addition salt of claim 1, wherein the rings in the unsaturated groups Z of formula (III) are chosen from pyridine, pyrimidine, pyrazine, oxazine, and triazine rings.

5. The compound or acid addition salt of claim 1, wherein two of the radicals $R_{10}$, $R_{11}$ and $R_{12}$ form a ring chosen from pyrrolidine, piperidine, piperazine and morpholine, said ring can be unsubstituted or substituted with a radical chosen from halogens, hydroxyl, $(C_1-C_6)$alkyls, $(C_1-C_6)$ monohydroxyalkyls, $(C_2-C_6)$polyhydroxyalkyls, nitro, cyano, cyano $(C_1-C_6)$alkyls, $(C_1-C_6)$alkoxys, tri$(C_1-C_6)$ alkylsilane $(C_1-C_6)$alkyls, amido, aldehydo, carboxyl, $(C_1-C_6)$alkylcarbonyls, thio, $(C_1-C_6)$thioalkyls, $(C_1-C_6)$ alkylthios, amino, and aminos protected with a radical chosen from $(C_1-C_6)$alkylcarbonyls, carbamyl, and $(C_1-C_6)$ alkylsulphonyls.

6. The compound or acid addition salt of claim 1, where X is chosen from halogens, hydroxide, hydrogenosulphates, and $(C_1-C_6)$alkyl sulphates.

7. The compound or acid addition salt of claim 1 chosen from:

1,3-bis{3-{3-[(2-aminoanilino)-N-propyl]}-3-H-imidazol-1-ium}propane dibromide, $N_1,N_3$-bis[3-N-(2-aminoanilino)propyl]-1,1,3,3-tetramethyldiammonium 1,3-propane dibromide, 1,4-bis{3-{2-[(2-aminoanilino)-N-ethyl]}-3-H-imidazol-1-ium}butane dichloride, 1-[2-(2-aminoanilino)ethyl]-3-[3-(2-aminoanilino)propyl]-3H-imidazol-1-ium monochloride, and the acid addition salts thereof.

8. The acid addition salt of claim 1 chosen from the hydrochlorides, hydrobromides, sulphates, citrates, succinates, tartrates, lactates, and acetates.

9. An oxidation base, coupler, or self-oxidizing dye for the oxidation dyeing of keratin fibres comprising a compound of formula (I) below or an acid addition salt thereof:

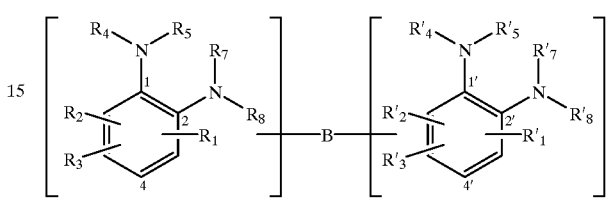

(I)

in which:
B is a linker arm chosen from linear and branched alkyl chains, which can be optionally interrupted with at least one group chosen from Z groups and hetero atoms, and which can be optionally substituted with at least one substituent chosen from hydroxyls and $(C_1-C_6)$ alkoxys, and which can optionally bear at least one ketone function;

$R_1$, $R_2$, $R_3$, $R'_1$, $R'_2$ and $R'_3$, which may be identical or different, can be the point of attachment of a linker arm B, otherwise, they are chosen from a hydrogen atom; halogens; Z groups; $(C_1-C_6)$alkylcarbonyls; amino $(C_1-C_6)$alkylcarbonyls; N—Z-amino$(C_1-C_6)$ alkylcarbonyls; N—$(C_1-C_6)$alkylamino$(C_1-C_6)$ alkylcarbonyls; N,N-di$(C_1-C_6)$alkylamino$(C_1-C_6)$ alkylcarbonyls; amino$(C_1-C_6)$alkylcarbonyl$(C_1-C_6)$ alkyls; N—Z-amino$(C_1-C_6)$alkylcarbonyl$(C_1-C_6)$ alkyls; N—$(C_1-C_6)$alkylamino$(C_1-C_6)$alkylcarbonyl $(C_1-C_6)$alkyls; N,N-di$(C_1-C_6)$alkylamino$(C_1-C_6)$ alkylcarbonyl$(C_1-C_6)$alkyls; carboxyl; $C_1-C_6)$ alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$ alkylaminosulphonyls; $(C_1-C_6)$aminosulphonylalkyls; $(C_1-C_6)$N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; carbamyl; N—$(C_1-C_6)$alkylcarbamyls; N,N-di$(C_1-C_6)$ alkylcarbamyls; carbamyl$(C_1-C_6)$alkyls; N—$(C_1-C_6)$ alkylcarbamyl$(C_1-C_6)$alkyls; N,N-di$(C_1-C_6)$ alkylcarbamyl$(C_1-C_6)$alkyls; $(C_1-C_6)$alkyls; $(C_1-C_6)$ monohydroxyalkyls; $(C_2-C_6)$polyhydroxyalkyls; $(C_1-C_6)$alkoxy$(C_1-C_6)$alkyls; $(C_1-C_6)$trifluoroalkyls; cyano; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$ alkylcarbonyls, amino$(C_1-C_6)$alkylcarbonyls, N—Z-amino$(C_1-C_6)$alkylcarbonyls, N—$(C_1-C_6)$alkylamino $(C_1-C_6)$alkylcarbonyls, N,N-di$(C_1-C_6)$alkylamino $(C_1-C_6)$alkylcarbonyls, $(C_1-C_6)$alkylcarboxyls, carbamyl, N—$(C_1-C_6)$alkylcarbamyls, N,N-di$(C_1-C_6)$ alkylcarbamyls, $(C_1-C_6)$alkylsulphonyls, aminosulphonyls, N—Z-aminosulphonyls, $(C_1-C_6)$N-alkylaminosulphonyl, N,N-di$(C_1-C_6)$ alkylaminosulphonyls, thiocarbamyl, formyl, and Z groups in which the linker arm B comprises a ketone function directly attached to the nitrogen atom of the amino group;

$R_6$ can be the point of attachment of a linker arm B, otherwise $R_6$ is a radical chosen from ($C_1$–$C_6$)alkyls; ($C_1$–$C_6$)monohydroxyalkyls; ($C_2$–$C_6$)polyhydroxyalkyls; Z groups; ($C_1$–$C_6$)alkoxy($C_1$–$C_6$)alkyls; aryls; benzyl; carboxy($C_1$–$C_6$)alkyls; ($C_1$–$C_6$)alkylcarboxy($C_1$–$C_6$)alkyls; cyano($C_1$–$C_6$)alkyls; carbamyl($C_1$–$C_6$)alkyls; N—($C_1$–$C_6$)alkylcarbamyl($C_1$–$C_6$)alkyls; N,N-di($C_1$–$C_6$)alkylcarbamyl($C_1$–$C_6$)alkyls; ($C_1$–$C_6$)trifluoroalkyls; ($C_1$–$C_6$)aminosulphonylalkyls; ($C_1$–$C_6$)N—Z-aminosulphonyl-alkyls; N—($C_1$–$C_6$)alkylaminosulphonyl($C_1$–$C_6$)alkyls; N,N-di($C_1$–$C_6$)alkylaminosulphonyl($C_1$–$C_6$)alkyls; ($C_1$–$C_6$)alkylsulphinyl($C_1$–$C_6$)alkyls; ($C_1$–$C_6$)alkylsulphonyl-($C_1$–$C_6$)alkyls; ($C_1$–$C_6$)alkylcarbonyl-($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$)monohydroxyalkyls, ($C_2$–$C_6$)polyhydroxyalkyls, ($C_1$–$C_6$)alkylcarbonyls, formyl, trifluoro-($C_1$–$C_6$)alkylcarbonyls, ($C_1$–$C_6$)alkylcarboxyls, carbamyl, N—($C_1$–$C_6$)alkylcarbamyls, N,N-di-($C_1$–$C_6$)alkylcarbamyls, thiocarbamyl, ($C_1$–$C_6$)alkylsulphonyls, and Z groups;

$R_4$, $R_5$, $R_7$, $R_8$, $R'_4$, $R'_5$, $R'_7$ and $R'_8$, which may be identical or different, can be the point of attachment of a linker arm B, otherwise they are chosen from a hydrogen atom; Z groups; ($C_1$–$C_6$)alkyls;($C_1$–$C_6$)monohydroxyalkyls; ($C_2$–$C_6$)polyhydroxyalkyls; ($C_1$–$C_6$)alkoxy($C_1$–$C_6$)alkyls; aryls; benzyl; cyano($C_1$–$C_6$)alkyls; carbamyl($C_1$–$C_6$)alkyls; N—($C_1$–$C_6$)alkylcarbamyl($C_1$–$C_6$)alkyls; N,N-di($C_1$–$C_6$)alkylcarbamyl($C_1$–$C_6$)alkyls; thiocarbamyl($C_1$–$C_6$)alkyls; ($C_1$–$C_6$)trifluoroalkyls; ($C_1$–$C_6$)sulphoalkyls; ($C_1$–$C_6$)alkylcarboxy($C_1$–$C_6$)alkyls; ($C_1$–$C_6$)alkylsulphinyl($C_1$–$C_6$)alkyls; ($C_1$–$C_6$)aminosulphonylalkyls; ($C_1$–$C_6$) N—Z-aminosulphonylalkyls; N—($C_1$–$C_6$)alkylaminosulphonyl($C_1$–$C_6$)alkyls; N,N-di($C_1$–$C_6$)alkylaminosulphonyl($C_1$–$C_6$)alkyls; ($C_1$–$C_6$)alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$)monohydroxyalkyls, ($C_2$–$C_6$)polyhydroxyalkyls, ($C_1$–$C_6$)alkylcarbonyls, carbamyl, N—($C_1$–$C_6$)alkylcarbamyls, N,N-di($C_1$–$C_6$)alkylcarbamyls, ($C_1$–$C_6$)alkylsulphonyls, formyls, trifluoro($C_1$–$C_6$)-alkylcarbonyls, ($C_1$–$C_6$)alkylcarboxyls, thiocarbamyl, and Z groups;

Z is chosen from unsaturated cationic groups of formulae (II) and (III) below, and saturated cationic groups of formula (IV) below:

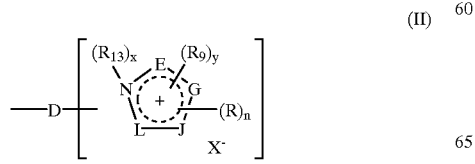
(II)

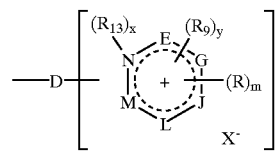
(III)

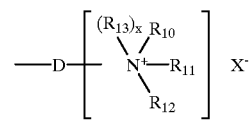
(IV)

in which:

D is a linker arm chosen from linear and branched alkyl chains, which are optionally interrupted by at least one hetero atom, and which can optionally be substituted with at least one radical chosen from hydroxyls and ($C_1$–$C_6$)alkoxys, and which also can optionally bear at least one ketone function;

the ring members E, G, J, L and M, which may be identical or different, are chosen from carbon, oxygen, sulphur and nitrogen atoms;

n is chosen from the integers 0, 1, 2, 3, and 4;

m is chosen from the integers 0, 1, 2, 3, 4, and 5;

the radicals R, which may be identical or different, can be the point of attachment of a linker arm B, otherwise they are chosen from a second group Z which is identical to or different from the first group Z, halogen atoms, a hydroxyl group, ($C_1$–$C_6$)alkyls, ($C_1$–$C_6$)monohydroxyalkyls, ($C_2$–$C_6$)polyhydroxyalkyls, nitro, cyano, cyano($C_1$–$C_6$)alkyls, ($C_1$–$C_6$)alkoxyls, tri($C_1$–$C_6$)alkylsilane($C_1$–$C_6$)alkyls, amido, aldehydo, carboxyl, ($C_1$–$C_6$)alkylcarbonyls, thio, ($C_1$–$C_6$)thioalkyls, ($C_1$–$C_6$)alkylthios, amino, aminos protected with a radical chosen from ($C_1$–$C_6$)alkylcarbonyls, carbamyl, and ($C_1$–$C_6$)alkylsulphonyls; and NHR″ and NR″R‴ groups in which R″ and R‴, which may be identical or different, are chosen from ($C_1$–$C_6$)alkyl radicals, ($C_1$–$C_6$)monohydroxyalkyl radicals and ($C_2$–$C_6$)polyhydroxyalkyl radicals;

$R_9$ can be the point of attachment of a linker arm B, otherwise $R_9$ is a radical chosen from ($C_1$–$C_6$)alkyls, ($C_1$–$C_6$)monohydroxyalkyls, ($C_2$–$C_6$)polyhydroxyalkyls, cyano($C_1$–$C_6$)alkyls, tri($C_1$–$C_6$)alkylsilane($C_1$–$C_6$)alkyls, ($C_1$–$C_6$)alkoxy($C_1$–$C_6$)alkyls, carbamyl-($C_1$–$C_6$)alkyls, ($C_1$–$C_6$)alkylcarboxy($C_1$–$C_6$)alkyls, benzyl, and a second group Z which is identical to or different from the first group Z;

$R_{10}$, $R_{11}$ and $R_{12}$, which may be identical or different, can be the point of attachment of a linker arm B, otherwise they are radicals chosen from ($C_1$–$C_6$) alkyls, ($C_1$–$C_6$) monohydroxyalkyls, ($C_2$–$C_6$) polyhydroxyalkyls, ($C_1$–$C_6$)alkoxy($C_1$–$C_6$)alkyls, cyano($C_1$–$C_6$)alkyls, aryls, benzyl, ($C_1$–$C_6$) amidoalkyls, tri($C_1$–$C_6$)alkylsilane($C_1$–$C_6$)alkyls, and ($C_1$–$C_6$)aminoalkyls in which the amine is protected with a radical chosen from ($C_1$–$C_6$) alkylcarbonyls, carbamyl, and ($C_1$–$C_6$) alkylsulphonyls; two of the radicals $R_{10}$, $R_{11}$ and $R_{12}$ can together also form, with the nitrogen atom to which they are attached, a saturated 5- or 6-membered ring or a ring containing at least one additional hetero atom, it being possible for the ring to be unsubstituted or to be substituted with a substituent chosen from halogen atoms, a hydroxyl group, $(C_1-C_6)$alkyls, $(C_1-C_6)$ monohydroxyalkyls, $(C_2-C_6)$polyhydroxyalkyls, nitro, cyano, cyano $(C_1-C_6)$alkyls, $(C_1-C_6)$ alkoxys, tri$(C_1-C_6)$ alkylsilane$(C_1-C_6)$alkyls, amido, aldehydo, carboxyl, keto$(C_1-C_6)$alkyls, thio, $(C_1-C_6)$ thioalkyls, $(C_1-C_6)$ alkylthios, amino, and aminos protected with a radical chosen from $(C_1-C_6)$ alkylcarbonyls, carbamyl, and $(C_1-C_6)$ alkylsulphonyls;

one of the radicals $R_{10}$, $R_{11}$ and $R_{12}$ can also be chosen from a second group Z which is identical to or different from the first group Z;

$R_{13}$ can be the point of attachment of a linker arm B, otherwise $R_{13}$ is a radical chosen from $(C_1-C_6)$ alkyls; $(C_1-C_6)$monohydroxyalkyls; $(C_2-C_6)$ polyhydroxyalkyls; aryls; benzyl; $(C_1-C_6)$ aminoalkyls, $(C_1-C_6)$aminoalkyls in which the amine is protected with a radical chosen from $(C_1-C_6)$alkylcarbonyls, carbamyl, and $(C_1-C_6)$ alkylsulphonyls; carboxy$(C_1-C_6)$alkyls; cyano $(C_1-C_6)$alkyls; carbamyl$(C_1-C_6)$alkyls; $(C_1-C_6)$ trifluoroalkyls; tri$(C_1-C_6)$alkylsilane-$(C_1-C_6)$alkyl radical; a $C_1-C_6$ sulphonamidoalkyl radical; $(C_1-C_6)$ alkylcarboxy$(C_1-C_6)$alkyls; $(C_1-C_6)$alkylsulphinyl $(C_1-C_6)$alkyls; $(C_1-C_6)$alkylsulphonyl$(C_1-C_6)$ alkyls; $(C_1-C_6)$alkylketo$(C_1-C_6)$alkyls; N—$(C_1-C_6)$alkylcarbamyl$(C_1-C_6)$alkyls; and N—$(C_1-C_6)$alkylsulphonamido$(C_1-C_6)$alkyls;

x and y are chosen from the integers 0 and 1; with the proviso that:

in the unsaturated cationic groups of formula (II):
when x=0, the linker arm D is attached to the nitrogen atom,
when x=1, the linker arm D is attached to one of the ring members E, G, J and L,
y can take the value 1 only:
1) when the ring members E, G, J and L simultaneously represent a carbon atom and when the radical $R_9$ is borne by the nitrogen atom of the unsaturated ring; or alternatively
2) when at least one of the ring members E, G, J and L represents a nitrogen atom to which the radical $R_9$ is attached;

in the unsaturated cationic groups of formula (III):
when x=0, the linker arm D is attached to the nitrogen atom,
when x=1, the linker arm D is attached to one of the ring members E, G, J, L and M,
y can take the value 1 only when at least one of the ring members E, G, J, L and M is chosen from divalent atoms and when the radical $R_9$ is borne by the nitrogen atom of the unsaturated ring;

in the cationic groups of formula (IV):
when x=0, then the linker arm D is attached to the nitrogen atom bearing the radicals $R_{10}$ to $R_{12}$,
when x=1, then two of the radicals $R_{10}$ to $R_{12}$ form, together with the nitrogen atom to which they are attached, a saturated 5- or 6-membered ring as defined above, and the linker arm D is borne by a carbon atom of the saturated ring;

$X^-$ is chosen from monovalent and divalent anions; it being understood that:
the number of cationic groups Z is at least equal to 1;

when at least one of $R_4$, $R_5$, $R'_4$, $R'_5$, $R_7$, $R_8$, $R'_7$, and $R'_8$ is chosen from Z groups in which the linker arm D is chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$;

when at least one of $R_4$, $R_5$, $R'_4$, $R'_5$, $R_7$, $R_8$, $R'_7$, and $R'_8$ is the point of a attachment of a linker arm B chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$.

10. A composition for the oxidation dyeing of keratin fibres, comprising a medium suitable for dyeing and at least one ingredient chosen from compounds of formula (I) below, and the addition salts thereof:

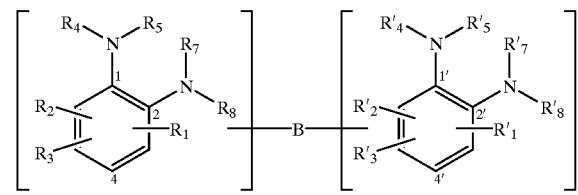

(I)

in which:

B is a linker arm chosen from linear and branched alkyl chains, which can be optionally interrupted with at least one group chosen from Z groups and hetero atoms, and which can be optionally substituted with at least one substituent chosen from hydroxyls and $(C_1-C_6)$ alkoxys, and which can optionally bear at least one ketone function;

$R_1$, $R_2$, $R_3$, $R'_1$, $R'_2$ and $R'_3$, which may be identical or different, can be the point of attachment of a linker arm B, otherwise, they are chosen from a hydrogen atom; halogens; Z groups; $(C_1-C_6)$alkylcarbonyls; amino $(C_1-C_6)$alkylcarbonyls; N—Z-amino$(C_1-C_6)$ alkylcarbonyls; N—$(C_1-C_6)$alkylamino$(C_1-C_6)$ alkylcarbonyls; N,N-di$(C_1-C_6)$alkylamino$(C_1-C_6)$ alkylcarbonyls; amino$(C_1-C_6)$alkylcarbonyl$(C_1-C_6)$-alkyls; N—Z-amino$(C_1-C_6)$alkylcarbonyl$(C_1-C_6)$ alkyls; N—$(C_1-C_6)$alkylamino$(C_1-C_6)$-alkylcarbonyl $(C_1-C_6)$alkyls; N,N-di$(C_1-C_6)$alkylamino$(C_1-C_6)$ alkylcarbonyl$(C_1-C_6)$alkyls; carboxyl; $C_1-C_6$ alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$ alkylaminosulphonyls; $(C_1-C_6)$aminosulphonylalkyls; $(C_1-C_6)$N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; carbamyl; N—$(C_1-C_6)$alkylcarbamyls; N,N-di$(C_1-C_6)$ alkylcarbamyls; carbamyl$(C_1-C_6)$alkyls; N—$(C_1-C_6)$ alkylcarbamyl$(C_1-C_6)$alkyls; N,N-di$(C_1-C_6)$ alkylcarbamyl$(C_1-C_6)$alkyls; $(C_1-C_6)$alkyls; $(C_1-C_6)$ monohydroxyalkyls; $(C_2-C_6)$polyhydroxyalkyls; $(C_1-C_8)$alkoxy$(C_1-C_8)$alkyls; $(C_1-C_5)$trifluoroalkyls; cyano; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$ alkylcarbonyls, amino$(C_1-C_6)$alkylcarbonyls, N—Z-amino$(C_1-C_6)$alkylcarbonyls, N—$(C_1-C_6)$alkylamino $(C_1-C_6)$alkylcarbonyls, N,N-di$(C_1-C_6)$alkylamino ($C_1$–$C_6$)alkylcarbonyls, ($C_1$–$C_6$)alkylcarboxyls, carbamyl, N—($C_1$–$C_6$)alkylcarbamyls, N,N-di($C_1$–$C_6$)alkylcarbamyls, ($C_1$–$C_6$)alkylsulphonyls, aminosulphonyls, N—Z-aminosulphonyls, ($C_1$–$C_6$)N-alkylaminosulphonyl, N,N-di($C_1$–$C_6$)alkylaminosulphonyls, thiocarbamyl, formyl, and Z groups in which the linker arm B comprises a ketone function directly attached to the nitrogen atom of the amino group;

$R_6$ can be the point of attachment of a linker arm B, otherwise $R_6$ is a radical chosen from ($C_1$–$C_6$)alkyls; ($C_1$–$C_6$)monohydroxyalkyls; ($C_2$–$C_6$)polyhydroxyalkyls; Z groups; ($C_1$–$C_6$)alkoxy($C_1$–$C_6$)alkyls; aryls; benzyl; carboxy($C_1$–$C_6$)alkyls; ($C_1$–$C_6$)alkylcarboxy($C_1$–$C_6$)alkyls; cyano($C_1$–$C_6$)alkyls; carbamyl($C_1$–$C_6$)alkyls; N—($C_1$–$C_6$)alkylcarbamyl($C_1$–$C_6$)alkyls; N,N-di($C_1$–$C_6$)alkylcarbamyl($C_1$–$C_6$)alkyls; ($C_1$–$C_6$)trifluoroalkyls; ($C_1$–$C_6$)aminosulphonylalkyls; ($C_1$–$C_6$)N—Z-aminosulphonyl-alkyls; N—($C_1$–$C_6$)alkylaminosulphonyl($C_1$–$C_6$)alkyls; N,N-di($C_1$–$C_6$)alkylaminosulphonyl($C_1$–$C_6$)alkyls; ($C_1$–$C_6$)alkylsulphinyl($C_1$–$C_6$)alkyls; ($C_1$–$C_6$)alkylsulphonyl-($C_1$–$C_6$)alkyls; ($C_1$–$C_6$)alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$)monohydroxyalkyls, ($C_2$–$C_6$)polyhydroxyalkyls, ($C_1$–$C_6$)alkylcarbonyls, formyl, trifluoro-($C_1$–$C_6$)alkylcarbonyls, ($C_1$–$C_6$)alkylcarboxyls, carbamyl, N—($C_1$–$C_6$)alkylcarbamyls, N,N-di-($C_1$–$C_6$)alkylcarbamyls, thiocarbamyl, ($C_1$–$C_6$)alkylsulphonyls, and Z groups;

$R_4$, $R_5$, $R_7$, $R_8$, $R'_4$, $R'_5$, $R'_7$ and $R'_8$, which may be identical or different, can be the point of attachment of a linker arm B, otherwise they are chosen from a hydrogen atom; Z groups; ($C_1$–$C_6$)alkyls;($C_1$–$C_6$)monohydroxyalkyls; ($C_2$–$C_6$) polyhydroxyalkyls; ($C_1$–$C_6$)alkoxy($C_1$–$C_6$)alkyls; aryls; benzyl; cyano($C_1$–$C_6$)alkyls; carbamyl($C_1$–$C_6$)alkyls; N—($C_1$–$C_6$)alkylcarbamyl($C_1$–$C_6$)alkyls; N,N-di($C_1$–$C_6$)alkylcarbamyl($C_1$–$C_6$)alkyls; thiocarbamyl($C_1$–$C_6$)alkyls; ($C_1$–$C_6$)trifluoroalkyls; ($C_1$–$C_6$)sulphoalkyls; ($C_1$–$C_6$)alkylcarboxy($C_1$–$C_6$)alkyls; ($C_1$–$C_6$)alkylsulphinyl($C_1$–$C_6$)alkyls; ($C_1$–$C_6$)aminosulphonylalkyls; ($C_1$–$C_6$) N—Z-aminosulphonylalkyls; N—($C_1$–$C_6$)alkylaminosulphonyl($C_1$–$C_6$)alkyls; N,N-di($C_1$–$C_6$)alkylaminosulphonyl($C_1$–$C_6$)alkyls; ($C_1$–$C_6$)alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$) monohydroxyalkyls, ($C_2$–$C_6$)polyhydroxyalkyls, ($C_1$–$C_6$)alkylcarbonyls, carbamyl, N—($C_1$–$C_6$)alkylcarbamyls, N,N-di($C_1$–$C_6$)alkylcarbamyls, ($C_1$–$C_6$)alkylsulphonyls, formyls, trifluoro($C_1$–$C_6$)-alkylcarbonyls, ($C_1$–$C_6$)alkylcarboxyls, thiocarbamyl, and Z groups;

Z is chosen from unsaturated cationic groups of formulae (II) and (III) below, and saturated cationic groups of formula (IV) below:

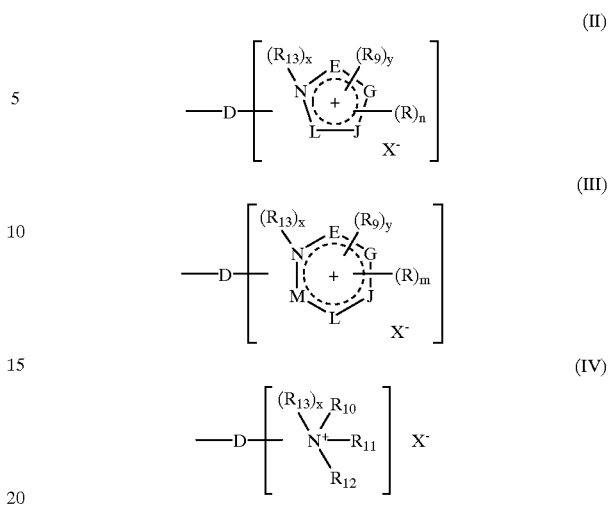

in which:
D is a linker arm chosen from linear and branched alkyl chains, which are optionally interrupted by at least one hetero atom, and which can optionally be substituted with at least one radical chosen from hydroxyls and ($C_1$–$C_6$)alkoxys, and which also can optionally bear at least one ketone function;
the ring members E, G, J, L and M, which may be identical or different, are chosen from carbon, oxygen, sulphur and nitrogen atoms;
n is chosen from the integers 0, 1, 2, 3, and 4;
m is chosen from the integers 0, 1, 2, 3, 4, and 5;
the radicals R, which may be identical or different, can be the point of attachment of a linker arm B, otherwise they are chosen from a second group Z which is identical to or different from the first group Z, halogen atoms, a hydroxyl group, ($C_1$–$C_6$)alkyls, ($C_1$–$C_6$)monohydroxyalkyls, ($C_2$–$C_6$)polyhydroxyalkyls, nitro, cyano, cyano($C_1$–$C_6$)alkyls, ($C_1$–$C_6$)alkoxyls, tri($C_1$–$C_6$)alkylsilane ($C_1$–$C_6$)alkyls, amido, aldehydo, carboxyl, ($C_1$–$C_6$)alkylcarbonyls, thio, ($C_1$–$C_6$)thioalkyls, ($C_1$–$C_6$)alkylthios, amino, aminos protected with a radical chosen from ($C_1$–$C_6$)alkylcarbonyls, carbamyl, and ($C_1$–$C_6$)alkylsulphonyls; and NHR" and NR"R'" groups in which R" and R'", which may be identical or different, are chosen from ($C_1$–$C_6$)alkyl radicals, ($C_1$–$C_6$)monohydroxyalkyl radicals and ($C_2$–$C_6$) polyhydroxyalkyl radicals;
$R_9$ can be the point of attachment of a linker arm B, otherwise $R_9$ is a radical chosen from ($C_1$–$C_6$)alkyls, ($C_1$–$C_6$)monohydroxyalkyls, ($C_2$–$C_6$) polyhydroxyalkyls, cyano($C_1$–$C_6$)alkyls, tri($C_1$–$C_6$) alkylsilane($C_1$–$C_6$)alkyls, ($C_1$–$C_6$)alkoxy($C_1$–$C_6$) alkyls, carbamyl-($C_1$–$C_6$)alkyls, ($C_1$–$C_6$) alkylcarboxy($C_1$–$C_6$)alkyls, benzyl, and a second group Z which is identical to or different from the first group Z;
$R_{10}$, $R_{11}$ and $R_{12}$, which may be identical or different, can be the point of attachment of a linker arm B, otherwise they are radicals chosen from ($C_1$–$C_6$) alkyls, ($C_1$–$C_6$) monohydroxyalkyls, ($C_2$–$C_6$) polyhydroxyalkyls, ($C_1$–$C_6$)alkoxy($C_1$–$C_6$)alkyls, cyano($C_1$–$C_6$)alkyls, aryls, benzyl, ($C_1$–$C_6$) amidoalkyls, tri($C_1$–$C_6$)alkylsilane($C_1$–$C_6$)alkyls, and ($C_1$–$C_6$)aminoalkyls in which the amine is protected with a radical chosen from $(C_1-C_6)$ alkylcarbonyls, carbamyl, and $(C_1-C_6)$ alkylsulphonyls; two of the radicals $R_{10}$, $R_{11}$ and $R_{12}$ can together also form, with the nitrogen atom to which they are attached, a saturated 5- or 6-membered ring or a ring containing at least one additional hetero atom, it being possible for the ring to be unsubstituted or to be substituted with a substituent chosen from halogen atoms, a hydroxyl group, $(C_1-C_6)$alkyls, $(C_1-C_6)$monohydroxyalkyls, $(C_2-C_6)$polyhydroxyalkyls, nitro, cyano, cyano $(C_1-C_6)$alkyls, $(C_1-C_6)$alkoxys, tri$(C_1-C_6)$alkylsilane$(C_1-C_6)$alkyls, amido, aldehydo, carboxyl, keto$(C_1-C_6)$alkyls, thio, $(C_1-C_6)$thioalkyls, $(C_1-C_6)$alkylthios, amino, and aminos protected with a radical chosen from $(C_1-C_6)$ alkylcarbonyls, carbamyl, and $(C_1-C_6)$ alkylsulphonyls;

one of the radicals $R_{10}$, $R_{11}$ and $R_{12}$ can also be chosen from a second group Z which is identical to or different from the first group Z;

$R_{13}$ can be the point of attachment of a linker arm B, otherwise $R_{13}$ is a radical chosen from $(C_1-C_6)$ alkyls; $(C_1-C_6)$monohydroxyalkyls; $(C_2-C_6)$ polyhydroxyalkyls; aryls; benzyl; $(C_1-C_6)$ aminoalkyls, $(C_1-C_6)$aminoalkyls in which the amine is protected with a radical chosen from $(C_1-C_6)$alkylcarbonyls, carbamyl, and $(C_1-C_6)$ alkylsulphonyls; carboxy$(C_1-C_6)$alkyls; cyano $(C_1-C_6)$alkyls; carbamyl$(C_1-C_6)$alkyls; $(C_1-C_6)$ trifluoroalkyl tri$(C_1-C_6)$alkylsilane-$(C_1-C_6)$alkyl radical; a $C_1-C_6$ sulphonamidoalkyl radical; $(C_1-C_6)$ alkylcarboxy$(C_1-C_6)$alkyls; $(C_1-C_6)$alkylsulphinyl $(C_1-C_6)$alkyls; $(C_1-C_6)$alkylsulphonyl$(C_1-C_6)$ alkyls; $(C_1-C_6)$alkylketo$(C_1-C_6)$alkyls; N—$(C_1-C_6)$alkylcarbamyl$(C_1-C_6)$alkyls; and N—$(C_1-C_6)$alkylsulphonamido$(C_1-C_6)$alkyls;

x and y are chosen from the integers 0 and 1; with the proviso that:
in the unsaturated cationic groups of formula (II):
when x=0, the linker arm D is attached to the nitrogen atom,
when x=1, the linker arm D is attached to one of the ring members E, G, J and L,
y can take the value 1 only:
1) when the ring members E, G, J and L simultaneously represent a carbon atom and when the radical $R_9$ is borne by the nitrogen atom of the unsaturated ring; or alternatively
2) when at least one of the ring members E, G, J and L represents a nitrogen atom to which the radical $R_9$ is attached;
in the unsaturated cationic groups of formula (III):
when x=0, the linker arm D is attached to the nitrogen atom,
when x=1, the linker arm D is attached to one of the ring members E, G, J, L and M,
y can take the value 1 only when at least one of the ring members E, G, J, L and M is chosen from divalent atoms and when the radical $R_9$ is borne by the nitrogen atom of the unsaturated ring;
in the cationic groups of formula (IV):
when x=0, then the linker arm D is attached to the nitrogen atom bearing the radicals $R_{10}$ to $R_{12}$,
when x=1, then two of the radicals $R_{10}$ to $R_{12}$ form, together with the nitrogen atom to which they are attached, a saturated 5- or 6-membered ring as defined above, and the linker arm D is borne by a carbon atom of the saturated ring;

$X^-$ is chosen from monovalent and divalent anions; it being understood that:
the number of cationic groups Z is at least equal to 1;
when at least one of $R_4$, $R_5$, $R'_4$, $R'_5$, $R_7$, $R_8$, $R'_7$, and $R'_8$ is chosen from Z groups in which the linker arm D is chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$;
when at least one of $R_4$, $R_5$, $R'_4$, $R'_5$, $R_7$, $R_8$, $R'_7$, and $R'_8$ is the point of a attachment of a linker arm B chosen from alkyl chains comprising a ketone function, then the ketone function is not directly attached to the nitrogen atom of the group —$NR_4R_5$, —$NR'_4R'_5$, —$NR_7R_8$ or —$NR_7R'_8$.

11. The dye composition of claim 10, wherein said at least one ingredient is present in said dye composition in an amount ranging from 0.0005 to 12% by weight relative to the total weight of said dye composition.

12. The dye composition of claim 11, wherein said at least one ingredient is present in said dye composition in an amount ranging from 0.005 to 6% by weight relative to the total weight of said dye composition.

13. The dye composition of claim 10, further comprising at least one oxidation base chosen from para-phenylenediamines, bis(phenyl)alkylenediamines, para-aminophenols, ortho-aminophenols, and heterocyclic bases other than said at least one compound of formula (I).

14. The dye composition of claim 13, wherein the para-phenylenediamenes are chosen from para-phenylenediamine, para-tolylene-diamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylene-diamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2β-hydroxyethyloxy-para-phenylenediamine, 2β-acetylaminoethyloxy-para-phenylenediamine and N-(β-methoxyethyl)-para-phenylenediamine, and the acid addition salts thereof.

15. The dye composition according to claim 13, wherein said bis(phenyl)alkylenediamines are chosen from N,N'-bis(β-hydroxyethyl)-N,N'-bis(4'-aminophenyl)-1,3-diaminopropanol, N,N'-bis(β-hydroxy-ethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)-tetramethylenediamine, N,N'-bis(4-methylaminophenyl)-tetramethylenediamine, N,N'-bis (ethyl)-N,N'-bis(4'-amino-3'-methylphenyl)ethylenediamine and 1,8-bis(2,5-diaminophenoxy)-3,5-dioxaoctane, and the acid addition salts thereof.

16. The dye composition of claim 13, wherein the para-aminophenols are chosen from para-aminophenol, 4-amino- 3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

17. The dye composition of claim 13, wherein the ortho-aminophenols are chosen from 2-aminophenol, 2-amino-5-methylphenol, 2-amino-6-methylphenol and 5-acetamid-2-aminophenol, and the acid addition salts thereof.

18. The dye composition of claim 13, wherein the heterocyclic bases other than said at least one compound of formula (I) are chosen from pyridine derivatives, pyrimidine derivatives and pyrazole derivatives.

19. The dye composition of claim 13, wherein said at least one oxidation base is present in said dye composition in an amount ranging from 0.0005 to 12% by weight relative to the total weight of the dye composition.

20. The dye composition of claim 19, wherein said at least one oxidation base is present in said dye composition in an amount ranging from 0.005 to 6% by weight relative to the total weight of the dye composition.

21. The dye composition of claim 10, further comprising at least one coupler chosen from meta-phenylenediamines, meta-aminophenols, meta-diphenols, and heterocyclic couplers other than said at least one compound of formula (I).

22. The dye composition of claim 21, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the acid addition salts thereof.

23. The dye composition of claim 21, wherein said at least one coupler is present in said dye composition in an amount ranging from 0.0001 to 10% by weight approximately relative to the total weight of the dye composition.

24. The dye composition of claim 23, wherein said at least one coupler is present in said dye composition in an amount ranging from 0.005 to 5% by weight approximately relative to the total weight of the dye composition.

25. The dye composition of claim 10, wherein said acid addition salts are chosen from hydrochlorides, hydrobromides, sulphates, citrates, succinates, tartrates, lactates, and acetates.

26. A process for the oxidation dyeing of keratin fibres comprising applying at least one dye composition to said fibres for a period which is sufficient to develop a desired coloration, either in air or with an oxidizing agent, wherein said at least one dye composition comprises at least one ingredient chosen from compounds of formula (I), and the acid addition salts thereof:

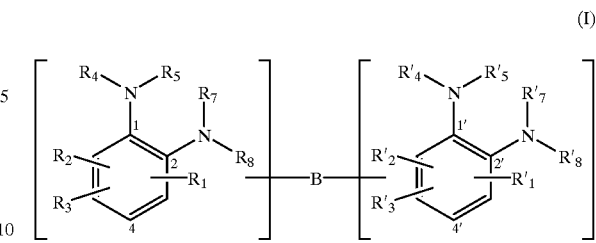
(I)

in which:

B is a linker arm chosen from linear and branched alkyl chains, which can be optionally interrupted with at least one group chosen from Z groups and hetero atoms, and which can be optionally substituted with at least one substituent chosen from hydroxyls and ($C_1$–$C_6$) alkoxys, and which can optionally bear at least one ketone function;

$R_1$, $R_2$, $R_3$, $R'_1$, $R'_2$ and $R'_3$, which may be identical or different, can be the point of attachment of a linker arm B, otherwise, they are chosen from a hydrogen atom; halogens; Z groups; ($C_1$–$C_6$)alkylcarbonyls; amino ($C_1$–$C_6$)alkylcarbonyls; N—Z-amino($C_1$–$C_6$) alkylcarbonyls; N—($C_1$–$C_6$)alkylamino($C_1$–$C_6$) alkylcarbonyls; N,N-di($C_1$–$C_6$)alkylamino($C_1$–$C_6$) alkylcarbonyls; amino($C_1$–$C_6$)alkylcarbonyl($C_1$–$C_6$) alkyls; N—Z-amino($C_1$–$C_6$)alkylcarbonyl($C_1$–$C_6$) alkyls; N—($C_1$–$C_6$)alkylamino($C_1$–$C_6$)alkylcarbonyl ($C_1$–$C_6$)alkyls; N,N-di($C_1$–$C_6$)alkylamino($C_1$–$C_6$) alkylcarbonyl($C_1$–$C_6$)alkyls; carboxyl;($C_1$–$C_6$) alkylcarboxyls; ($C_1$–$C_6$)alkylsulphonyls; aminosulphonyls; N—Z-amino-sulphonyls; ($C_1$–$C_6$)N-alkylaminosulphonyls; N,N-di($C_1$–$C_6$) alkylaminosulphonyls; ($C_1$–$C_6$)aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; carbamyl; N—($C_1$–$C_6$)alkylcarbamyls; N,N-di($C_1$–$C_6$) alkylcarbamyls; carbamyl($C_1$–$C_6$)alkyls; N—($C_1$–$C_6$) alkylcarbamyl($C_1$–$C_6$)alkyls; N,N-di($C_1$–$C_6$) alkylcarbamyl($C_1$–$C_6$)alkyls; ($C_1$–$C_6$)alkyls; ($C_1$–$C_6$) monohydroxyalkyls; ($C_2$–$C_6$)polyhydroxyalkyls; ($C_1$–$C_6$)alkoxy($C_1$–$C_6$)alkyls; ($C_1$–$C_6$)trifluoroalkyls; cyano; $OR_6$ and $SR_6$ groups; amino groups protected with a radical chosen from ($C_1$–$C_6$)alkylcarbonyls, ($C_1$–$C_6$)alkylcarboxyls, trifluoro($C_1$–$C_6$) alkylcarbonyls, amino($C_1$–$C_6$)alkylcarbonyls, N—Z-amino($C_1$–$C_6$)alkylcarbonyls, N—($C_1$–$C_6$)alkylamino ($C_1$–$C_6$)alkylcarbonyls, N,N-di($C_1$–$C_6$)alkylamino ($C_1$–$C_6$)alkylcarbonyls, ($C_1$–$C_6$)alkylcarboxyls, carbamyl, N—($C_1$–$C_6$)alkylcarbamyls, N,N-di($C_1$–$C_6$) alkylcarbamyls, ($C_1$–$C_6$)alkylsulphonyls, aminosulphonyls, N—Z-aminosulphonyls, ($C_1$–$C_6$)N-alkylaminosulphonyl, N,N-di($C_1$–$C_6$) alkylaminosulphonyls, thiocarbamyl, formyl, and Z groups in which the linker arm B comprises a ketone function directly attached to the nitrogen atom of the amino group;

$R_6$ can be the point of attachment of a linker arm B, otherwise $R_6$ is a radical chosen from ($C_1$–$C_6$)alkyls; ($C_1$–$C_6$)monohydroxyalkyls; ($C_2$–$C_6$) polyhydroxyalkyls; Z groups; ($C_1$–$C_6$)alkoxy($C_1$–$C_6$) alkyls; aryls; benzyl; carboxy($C_1$–$C_6$)alkyls; ($C_1$–$C_6$) alkylcarboxy($C_1$–$C_6$)alkyls; cyano($C_1$–$C_6$)alkyls;

carbamyl($C_1$–$C_6$)alkyls; N—($C_1$–$C_6$)alkylcarbamyl($C_{1-96}$)alkyls; N,N-di($C_1$–$C_6$)alkylcarbamyl($C_1$–$C_6$)alkyls; ($C_1$–$C_6$)trifluoroalkyls; ($C_1$–$C_6$)aminosulphonylalkyls; ($C_1$–$C_6$)N—Z-aminosulphonylalkyls; N—($C_1$–$C_6$)alkylaminosulphonyl($C_1$–$C_6$)alkyls; N,N-di($C_1$–$C_6$)alkylaminosulphonyl($C_1$–$C_6$)alkyls; ($C_1$–$C_6$)alkylsulphinyl-($C_1$–$C_6$)alkyls;($C_1$–$C_6$)alkylsulphonyl-($C_1$–$C_6$)alkyls;($C_1$–$C_6$)alkylcarbonyl-($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$)monohydroxyalkyls, ($C_2$–$C_6$) polyhydroxyalkyls, ($C_1$–$C_6$)alkylcarbonyls, formyl, trifluoro-($C_1$–$C_6$)alkylcarbonyls, ($C_1$–$C_6$)alkylcarboxyls, carbamyl, N—($C_1$–$C_6$)alkylcarbamyls, N,N-di-($C_1$–$C_6$)alkylcarbamyls, thiocarbamyl, ($C_1$–$C_6$)alkylsulphonyls, and Z groups;

$R_4$, $R_5$, $R_7$, $R_8$, $R'_4$, $R'_5$, $R'_7$ and $R'_8$, which may be identical or different, can be the point of attachment of a linker arm B, otherwise they are chosen from a hydrogen atom; Z groups; ($C_1$–$C_6$)alkyls;($C_1$–$C_6$)monohydroxyalkyls; ($C_2$–$C_6$)polyhydroxyalkyls; ($C_1$–$C_6$)alkoxy($C_1$–$C_6$)alkyls; aryls; benzyl; cyano ($C_1$–$C_6$)alkyls; carbamyl($C_1$–$C_6$)alkyls; N—($C_1$–$C_6$)alkylcarbamyl($C_1$–$C_6$)alkyls; N,N-di($C_1$–$C_6$)alkylcarbamyl($C_1$–$C_6$)alkyls; thiocarbamyl($C_1$–$C_6$)alkyls; ($C_1$–$C_6$)trifluoroalkyls; ($C_1$–$C_6$)sulphoalkyls; ($C_1$–$C_6$)alkylcarboxy($C_1$–$C_6$)alkyls; ($C_1$–$C_6$)alkylsulphinyl($C_1$–$C_6$)alkyls; ($C_1$–$C_6$)aminosulphonylalkyls; ($C_1$–$C_6$) N—Z-aminosulphonylalkyls; N—($C_1$–$C_6$)alkylaminosulphonyl($C_1$–$C_6$)alkyls; N,N-di($C_1$–$C_6$)alkylaminosulphonyl($C_1$–$C_6$)alkyls; ($C_1$–$C_6$)alkylcarbonyl($C_1$–$C_6$)alkyls; ($C_1$–$C_6$)aminoalkyls; ($C_1$–$C_6$) aminoalkyls in which the amine is substituted with one or two identical or different radicals chosen from ($C_1$–$C_6$)alkyls, ($C_1$–$C_6$) monohydroxyalkyls, ($C_2$–$C_6$)polyhydroxyalkyls, ($C_1$–$C_6$)alkylcarbonyls, carbamyl, N—($C_1$–$C_6$)alkylcarbamyls, N,N-di($C_1$–$C_6$)alkylcarbamyls, ($C_1$–$C_6$)alkylsulphonyls, formyls, trifluoro($C_1$–$C_6$)-alkylcarbonyls, ($C_1$–$C_6$)alkylcarboxyls, thiocarbamyl, and Z groups;

Z is chosen from unsaturated cationic groups of formulae (II) and (III) below, and saturated cationic groups of formula (IV) below:

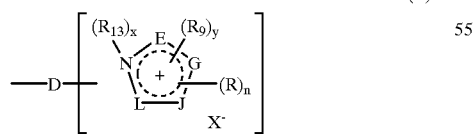

(II)

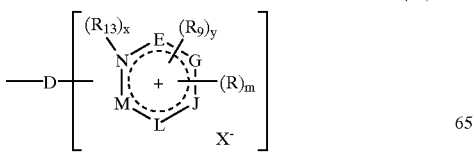

(III)

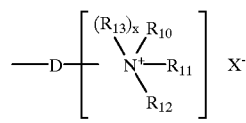

(IV)

in which:

D is a linker arm chosen from linear and branched alkyl chains, which are optionally interrupted by at least one hetero atom, and which can optionally be substituted with at least one radical chosen from hydroxyls and ($C_1$–$C_6$)alkoxys, and which also can optionally bear at least one ketone function;

the ring members E, G, J, L and M, which may be identical or different, are chosen from carbon, oxygen, sulphur and nitrogen atoms;

n is chosen from the integers 0, 1, 2, 3, and 4;

m is chosen from the integers 0, 1, 2, 3, 4, and 5;

the radicals R, which may be identical or different, can be the point of attachment of a linker arm B, otherwise they are chosen from a second group Z which is identical to or different from the first group Z, halogen atoms, a hydroxyl group, ($C_1$–$C_6$)alkyls, ($C_1$–$C_6$)monohydroxyalkyls, ($C_2$–$C_6$)polyhydroxyalkyls, nitro, cyano, cyano($C_1$–$C_6$)alkyls, ($C_1$–$C_6$)alkoxyls, tri($C_1$–$C_6$)alkylsilane($C_1$–$C_6$)alkyls, amidos, aldehydo, carboxyl, ($C_1$–$C_6$)alkylcarbonyls, thio, ($C_1$–$C_6$)thioalkyls, ($C_1$–$C_6$)alkylthios, amino, aminos protected with a radical chosen from ($C_1$–$C_6$)alkylcarbonyls, carbamyl, and ($C_1$–$C_6$)alkylsulphonyls; and NHR" and NR'R"' groups in which R" and R'", which may be identical or different, are chosen from ($C_1$–$C_6$)alkyl radicals, ($C_1$–$C_6$)monohydroxyalkyl radicals and ($C_2$–$C_6$) polyhydroxyalkyl radicals;

can be the point of attachment of a linker arm B, otherwise $R_9$ is a radical chosen from ($C_1$–$C_6$) alkyls, ($C_1$–$C_6$)monohydroxyalkyls, ($C_2$–$C_6$) polyhydroxyalkyls, cyano($C_1$–$C_6$)alkyls, tri($C_1$–$C_6$) alkylsilane($C_1$–$C_6$)alkyls, ($C_1$–$C_6$)alkoxy($C_1$–$C_6$) alkyls, carbamyl-($C_1$–$C_6$)alkyls, ($C_1$–$C_6$) alkylcarboxy($C_1$–$C_6$)-alkyls, benzyl, and a second group Z which is identical to or different from the first group Z;

$R_{10}$, $R_{11}$, and $R_{12}$, which may be identical or different, can be the point of attachment of a linker arm B, otherwise they are radicals chosen from ($C_1$–$C_6$) alkyls, ($C_1$–$C_6$) monohydroxyalkyls, ($C_2$–$C_6$) polyhydroxyalkyls, ($C_1$–$C_6$)alkoxy($C_1$–$C_6$)alkyls, cyano($C_1$–$C_6$)alkyls, aryls, benzyl, ($C_1$–$C_6$) amidoalkyls, tri($C_1$–$C_6$)alkylsilane($C_1$–$C_6$)alkyls, and ($C_1$–$C_6$)aminoalkyls in which the amine is protected with a radical chosen from ($C_1$–$C_6$) alkylcarbonyls, carbamyl, and ($C_1$–$C_6$) alkylsulphonyls; two of the radicals $R_{10}$, $R_{11}$ and $R_{12}$ can together also form, with the nitrogen atom to which they are attached, a saturated 5- or 6-membered ring or a ring containing at least one additional hetero atom, it being possible for the ring to be unsubstituted or to be substituted with a substituent chosen from halogen atoms, a hydroxyl group, ($C_1$–$C_6$) alkyls, ($C_1$–$C_6$)monohydroxyalkyls, ($C_2$–$C_6$) polyhydroxyalkyls, nitro, cyano, cyano($C_1$–$C_6$) alkyls, ($C_1$–$C_6$)alkoxys, tri($C_1$–$C_6$)alkylsilane ($C_1$–$C_6$)alkyls, amido, aldehydo, carboxyl, keto ($C_1$–$C_6$)alkyls, thio, ($C_1$–$C_6$)thioalkyls, ($C_1$–$C_6$) alkylthios, amino, and aminos protected with a radical chosen from ($C_1$–$C_6$)alkylcarbonyls, carbamyl, and ($C_1$–$C_6$)alkylsulphonyls;

one of the radicals $R_{10}$, $R_{11}$ and $R_{12}$ can also be chosen from a second group Z which is identical to or different from the first group Z;

$R_{13}$ can be the point of attachment of a linker arm B, otherwise $R_{13}$ is a radical chosen from ($C_1$–$C_6$) alkyls; ($C_1$–$C_6$)monohydroxy-alkyls; ($C_2$–$C_6$) polyhydroxyalkyls; aryls; benzyl; ($C_1$–$C_6$) aminoalkyls, ($C_1$–$C_6$)aminoalkyls in which the amine is protected with a radical chosen from ($C_1$–$C_6$)alkylcarbonyls, carbamyl, and ($C_1$–$C_6$) alkylsulphonyls; carboxy($C_1$–$C_6$)alkyls; cyano ($C_1$–$C_6$)alkyls; carbamyl($C_1$–$C_6$)alkyls; ($C_1$–$C_6$) trifluoroalkyls; tri($C_1$–$C_6$)alkylsilane-($C_1$–$C_6$)alkyl radical; a $C_1$–$C_6$ sulphonamidoalkyl radical; a ($C_1$–$C_6$)alkylcarboxy($C_1$–$C_6$)alkyls; ($C_1$–$C_6$) alkylsulphinyl($C_1$–$C_6$)alkyls; ($C_1$–$C_6$) alkylsulphonyl($C_1$–$C_6$)alkyls; ($C_1$–$C_6$)alkylketo ($C_1$–$C_6$)alkyls; N—($C_1$–$C_6$)alkylcarbamyl($C_1$–$C_6$) alkyls; N—($C_1$–$C_6$)alkylsulphonamido($C_1$–$C_6$) alkyls;

x and y are chosen from the integers 0 and 1; with the proviso that:

in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_9$ is borne by the nitrogen atom of the unsaturated ring; or alternatively
2) when at least one of the ring members E, G, J and L represents a nitrogen atom to which the radical $R_9$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical $R_9$ is borne by the nitrogen atom of the unsaturated ring;

in the cationic groups of formula (IV):
when x=0, then the linker arm D is attached to the nitrogen atom bearing the radicals $R_{10}$ to $R_{12}$,
when x=1, then two of the radicals $R_{10}$ to $R_{12}$ form, together with the nitrogen atom to which they are attached, a saturated 5- or 6-membered ring as defined above, and the linker arm D is borne by a carbon atom of the saturated ring;

$X^-$ is chosen from monovalent and divalent anions; it being understood that:
the number of cationic groups Z is at least equal to 1;
when at least one of $R_4$, $R_5$, $R'_4$, $R'_5$, $R_7$, $R_8$, $R'_7$, and $R'_8$ is chosen from Z groups which the linker arm D is chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$;
when at least one of $R_4$, $R_5$, $R'_4$, $R'_5$, $R_7$, $R_8$, $R'_7$, and $R'_8$ is the point of a attachment of a linker arm B chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$.

27. The process of claim 26, wherein said applying step is carried out by contact with air without addition of an oxidizing agent.

28. The process according to claim 27, wherein the coloration is developed at acidic, neutral or alkaline pH with an oxidizing agent which is added to the dye composition at a time just prior to applying said dye composition to said fibres, or which is present in an oxidizing composition which is applied to said keratin fibres simultaneously with said dye composition or sequentially in a separate manner from said dye composition.

29. The process according to claim 28, wherein said oxidizing agent is chosen from hydrogen peroxide, urea peroxide, alkali metal bromates, persalts, and enzymes.

30. The process according to claim 29, wherein the persalts are chosen from perborates and persulphates, and the enzymes are chosen from peroxidases and 2-electron oxidoreductases.

31. A multi-compartment dyeing device or multi-compartment dyeing kit, comprising, a first compartment containing at least one dye composition, and a second compartment containing at least one oxidizing composition, wherein said at least one dye composition comprises at least one ingredient chosen from compounds of formula (I), below, and acid addition salts thereof:

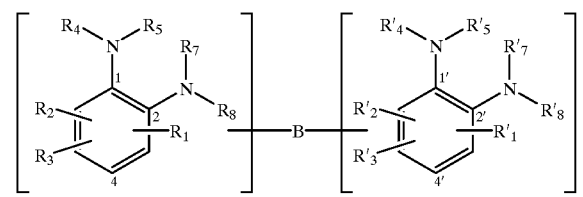

(I)

in which:
B is a linker arm chosen from linear arid branched alkyl chains, which can be optionally interrupted with at least one group chosen from Z groups and hetero atoms, and which can be optionally substituted with at least one substituent chosen from hydroxyls and ($C_1$–$C_6$) alkoxys, and which can optionally bear at least one ketone function;
$R_1$, $R_2$, $R_3$, $R'_1$, $R'_2$ and $R'_3$, which may be identical or different, can be the point of attachment of a linker arm B, otherwise, they are chosen from a hydrogen atom; halogens; Z groups; ($C_1$–$C_6$)alkylcarbonyls; amino ($C_1$–$C_6$)alkylcarbonyls; N—Z-amino($C_1$–$C_6$) alkylcarbonyls; N—($C_1$–$C_6$)alkylamino($C_1$–$C_6$) alkylcarbonyls; N,N-di($C_1$–$C_6$)alkylamino($C_1$–$C_6$) alkylcarbonyls; amino($C_1$–$C_6$)alkylcarbonyl($C_1$–$C_6$) alkyls; N—Z-amino($C_1$–$C_6$)alkylcarbonyl($C_1$–$C_6$) alkyls; N—($C_1$–$C_6$)alkylamino($C_1$–$C_6$)alkylcarbonyl ($C_1$–$C_6$)alkyls; N,N-di($C_1$–$C_6$)alkylamino($C_1$–$C_6$) alkylcarbonyl($C_1$–$C_6$)alkyls; carboxyl; $C_1$–$C_6$) alkylcarboxyls; ($C_1$–$C_6$)alkylsulphonyls; aminosulphonyls; N—Z-aminosulphonyls; ($C_1$–$C_6$)N-alkylaminosulphonyls; N,N-di($C_1$–$C_6$) alkylaminosulphonyls; ($C_1$–$C_6$)aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$)

alkylaminosulphonyl($C_1$–$C_6$)alkyls; carbamyl; N—($C_1$–$C_6$)alkylcarbamyls; N,N-di($C_1$–$C_6$) alkylcarbamyls; carbamyl($C_1$–$C_6$)alkyls; N—($C_1$–$C_6$) alkylcarbamyl($C_1$–$C_6$)alkyls; N,N-di($C_1$–$C_6$) alkylcarbamyl($C_1$–$C_6$)alkyls; ($C_1$–$C_6$)alkyls; ($C_1$–$C_6$) monohydroxyalkyls; ($C_2$–$C_6$)polyhydroxyalkyls; ($C_1$–$C_6$)alkoxy($C_1$–$C_6$)alkyls; ($C_1$–$C_6$)trifluoroalkyls; cyano; $OR_6$ and $SR_6$ groups; amino groups protected with a radical chosen from ($C_1$–$C_6$)alkylcarbonyls, ($C_1$–$C_6$)alkylcarboxyls, trifluoro($C_1$–$C_6$) alkylcarbonyls, amino($C_1$–$C_6$)alkylcarbonyls, N—Z-amino($C_1$–$C_6$)alkylcarbonyls, N—($C_1$–$C_6$)alkylamino($C_1$–$C_6$)alkylcarbonyls, N,N-di($C_1$–$C_6$)alkylamino($C_1$–$C_6$)alkylcarbonyls, ($C_1$–$C_6$)alkylcarboxyls, carbamyl, N—($C_1$–$C_6$)alkylcarbamyls, N,N-di($C_1$–$C_6$) alkylcarbamyls, ($C_1$–$C_6$)alkylsulphonyls, aminosulphonyls, N—Z-aminosulphonyls, ($C_1$–$C_6$)N-alkylaminosulphonyl, N,N-di($C_1$–$C_6$) alkylaminosulphonyls, thiocarbamyl, formyl, and Z groups in which the linker arm B comprises a ketone function directly attached to the nitrogen atom of the amino group;

$R_6$ can be the point of attachment of a linker arm B, otherwise $R_6$ is a radical chosen from ($C_1$–$C_6$)alkyls; ($C_1$–$C_6$)monohydroxyalkyls; ($C_2$–$C_6$) polyhydroxyalkyls; Z groups; ($C_1$–$C_6$)alkoxy($C_1$–$C_6$) alkyls; aryls; benzyl; carboxy($C_1$–$C_6$)alkyls; ($C_1$–$C_6$) alkylcarboxy($C_1$–$C_6$)alkyls; cyano($C_1$–$C_6$)alkyls; carbamyl($C_1$–$C_6$)alkyls; N—($C_1$–$C_6$)alkylcarbamyl ($C_1$–$C_6$)alkyls; N,N-di($C_1$–$C_6$)alkylcarbamyl($C_1$–$C_6$) alkyls; ($C_1$–$C_6$)trifluoroalkyls; ($C_1$–$C_6$) aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; ($C_1$–$C_6$) alkylsulphinyl($C_1$–$C_6$)alkyls;($C_1$–$C_6$)alkylsulphonyl-($C_1$–$C_6$)alkyls;($C_1$–$C_6$)alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$) monohydroxyalkyls, ($C_2$–$C_6$)polyhydroxyalkyls, ($C_1$–$C_6$)alkylcarbonyls, formyl, trifluoro-($C_1$–$C_6$) alkylcarbonyls, ($C_1$–$C_6$)alkylcarboxyls, carbamyl, N—($C_1$–$C_6$)alkylcarbamyls, N,N-di-($C_1$–$C_6$) alkylcarbamyls, thiocarbamyl, ($C_1$–$C_6$) alkylsulphonyls, and Z groups;

$R_4$, $R_5$, $R_7$, $R_8$, $R'_4$, $R'_5$, $R'_7$ and $R'_8$, which may be identical or different, can be the point of attachment of a linker arm B, otherwise they are chosen from a hydrogen atom; Z groups; ($C_1$–$C_6$) alkyls;($C_1$–$C_6$) monohydroxyalkyls; ($C_2$–$C_6$) polyhydroxyalkyls; ($C_1$–$C_6$)alkoxy($C_1$–$C_6$)alkyls; aryls; benzyl; cyano ($C_1$–$C_6$)alkyls; carbamyl($C_1$–$C_6$)alkyls; N—($C_1$–$C_6$) alkylcarbamyl($C_1$–$C_6$)alkyls; N,N-di($C_1$–$C_6$) alkylcarbamyl($C_1$–$C_6$)alkyls; thiocarbamyl($C_1$–$C_6$) alkyls; ($C_1$–$C_6$)trifluoroalkyls; ($C_1$–$C_6$)sulphoalkyls; ($C_1$–$C_6$)alkylcarboxy($C_1$–$C_6$)alkyls; ($C_1$–$C_6$) alkylsulphinyl($C_1$–$C_6$)alkyls; ($C_1$–$C_6$) aminosulphonylalkyls; ($C_1$–$C_6$)N—Z-aminosulphonylalkyls; N—($C_1$–$C_6$) alkylaminosulphonyl($C_1$–$C_6$)alkyls; N,N-di($C_1$–$C_6$) alkylaminosulphonyl($C_1$–$C_6$)alkyls; ($C_1$–$C_6$) alkylcarbonyl($C_1$–$C_6$)alkyls; ($C_1$–$C_6$)aminoalkyls; ($C_1$–$C_6$)aminoalkyls in which the amine is substituted with one or two identical or different radicals chosen from ($C_1$–$C_6$)alkyls, ($C_1$–$C_6$) monohydroxyalkyls, ($C_2$–$C_6$)polyhydroxyalkyls, ($C_1$–$C_6$)alkylcarbonyls, carbamyl, N—($C_1$–$C_6$)alkylcarbamyls, N,N-di($C_1$–$C_6$) alkylcarbamyls, ($C_1$–$C_6$)alkylsulphonyls, formyls, trifluoro($C_1$–$C_6$)-alkylcarbonyls, ($C_1$–$C_6$) alkylcarboxyls, thiocarbamyl, and Z groups;

Z is chosen from unsaturated cationic groups of formulae (II) and (III) below, and saturated cationic groups of formula (IV) below:

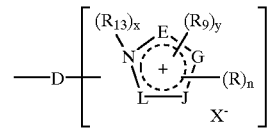

(II)

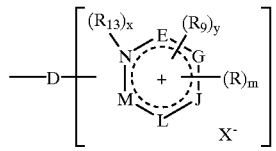

(III)

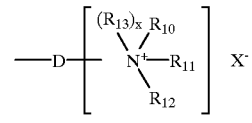

(IV)

in which:

D is a linker arm chosen from linear and branched alkyl chains, which are optionally interrupted by at least one hetero atom, and which can optionally be substituted with at least one radical chosen from hydroxyls and ($C_1$–$C_6$)alkoxys, and which also can optionally bear at least one ketone function;

the ring members E, G, J, L and M, which may be identical or different, are chosen from carbon, oxygen, sulphur and nitrogen atoms;

n is chosen from the integers 0, 1, 2, 3, and 4;

m is chosen from the integers 0, 1, 2, 3, 4, and 5;

the radicals R, which may be identical or different, can be the point of attachment of a linker arm B, otherwise they are chosen from a second group Z which is identical to or different from the first group Z, halogen atoms, a hydroxyl group, ($C_1$–$C_6$)alkyls, ($C_1$–$C_6$)monohydroxyalkyls, ($C_2$–$C_6$) polyhydroxyalkyls, nitro, cyano, cyano($C_1$–$C_6$) alkyls, ($C_1$–$C_6$)alkoxyls, tri($C_1$–$C_6$)alkylsilane ($C_1$–$C_6$)alkyls, amido, aldehydo, carboxyl, ($C_1$–$C_6$) alkylcarbonyls, thio, ($C_1$–$C_6$)thioalkyls, ($C_1$–$C_6$) alkylthios, amino, aminos protected with a radical chosen from ($C_1$–$C_6$)alkylcarbonyls, carbamyl, and ($C_1$–$C_6$)alkylsulphonyls; and NHR" and NR"R'" groups in which R" and R'", which may be identical or different, are chosen from ($C_1$–$C_6$)alkyl radicals, ($C_1$–$C_6$)monohydroxyalkyl radicals and ($C_2$–$C_6$) polyhydroxyalkyl radicals;

$R_9$ can be the point of attachment of a linker arm B, otherwise $R_9$ is a radical chosen from ($C_1$–$C_6$)alkyls, ($C_1$–$C_6$)monohydroxyalkyls, ($C_2$–$C_6$) polyhydroxyalkyls, cyano($C_1$–$C_6$)alkyls, tri($C_1$–$C_6$) alkylsilane($C_1$–$C_6$)alkyls, ($C_1$–$C_6$)alkoxy($C_1$–$C_6$) alkyls, carbamyl-($C_1$–$C_6$)alkyls, ($C_1$–$C_6$)alkylcarboxy ($C_1$–$C_6$)alkyls, benzyl, and a second group Z which is identical to or different from the first group Z;

$R_{10}$, $R_{11}$ and $R_{12}$, which may be identical or different, can be the point of attachment of a linker arm B, otherwise they are radicals chosen from $(C_1-C_6)$ alkyls, $(C_1-C_6)$ monohydroxyalkyls, $(C_2-C_6)$ polyhydroxyalkyls, $(C_1-C_6)$alkoxy$(C_1-C_6)$alkyls, cyano$(C_1-C_6)$alkyls, aryls, benzyl, $(C_1-C_6)$ amidoalkyls, tri$(C_1-C_6)$alkylsilane$(C_1-C_6)$alkyls, and $(C_1-C_6)$aminoalkyls in which the amine is protected with a radical chosen from $(C_1-C_6)$ alkylcarbonyls, carbamyl, and $(C_1-C_6)$ alkylsulphonyls; two of the radicals $R_{10}$, $R_{11}$ and $R_{12}$ can together also form, with the nitrogen atom to which they are attached, a saturated 5- or 6-membered ring or a ring containing at least one additional hetero atom, it being possible for the ring to be unsubstituted or to be substituted with a substituent chosen from halogen atoms, a hydroxyl group, $(C_1-C_6)$alkyls, $(C_1-C_6)$ monohydroxyalkyls, $(C_2-C_6)$polyhydroxyalkyls, nitro, cyano, cyano $(C_1-C_6)$alkyls, $(C_1-C_6)$ alkoxys, tri$(C_1-C_6)$ alkylsilane$(C_1-C_6)$alkyls, amido, aldehydo, carboxyl, keto$(C_1-C_6)$alkyls, thio, $(C_1-C_6)$ thioalkyls, $(C_1-C_6)$alkylthios, amino, and aminos protected with a radical chosen from $(C_1-C_6)$ alkylcarbonyls, carbamyl, and $(C_1-C_6)$ alkylsulphonyls;

one of the radicals $R_{10}$, $R_{11}$ and $R_{12}$ can also be chosen from a second group Z which is identical to or different from the first group Z;

$R_{13}$ can be the point of attachment of a linker arm B, otherwise $R_{13}$ is a radical chosen from $(C_1-C_6)$ alkyls; $(C_1-C_6)$monohydroxyalkyls; $(C_2-C_6)$ polyhydroxyalkyls; aryls; benzyl; $(C_1-C_6)$ aminoalkyls, $(C_1-C_6)$aminoalkyls in which the amine is protected with a radical chosen from $(C_1-C_6)$alkylcarbonyls, carbamyl, and $(C_1-C_6)$ alkylsulphonyls; carboxy$(C_1-C_6)$alkyls; cyano $(C_1-C_6)$alkyls; carbamyl$(C_1-C_6)$alkyls; $(C_1-C_6)$ trifluoroalkyls; tri$(C_1-C_6)$alkylsilane-$(C_1-C_6)$alkyl radical; a $C_1-C_6$ sulphonamidoalkyl radical; $(C_1-C_6)$ alkylcarboxy$(C_1-C_6)$alkyls; $(C_1-C_6)$alkylsulphinyl $(C_1-C_6)$alkyls; $(C_1-C_6)$alkylsulphonyl$(C_1-C_6)$ alkyls; $(C_1-C_6)$alkylketo$(C_1-C_6)$alkyls; N—$(C_1-C_6)$alkylcarbamyl$(C_1-C_6)$alkyls; and N—$(C_1-C_6)$alkylsulphonamido$(C_1-C_6)$alkyls;

x and y are chosen from the integers 0 and 1; with the proviso that:

in the unsaturated cationic groups of formula (II):

when x=0, the linker arm D is attached to the nitrogen atom, when x=1, the linker arm D is attached to one of the ring members E, G, J and L, y can take the value 1 only:
1) when the ring members E, G, J and L simultaneously represent a carbon atom and when the radical $R_9$ is borne by the nitrogen atom of the unsaturated ring; or alternatively
2) when at least one of the ring members E, G, J and L represents a nitrogen atom to which the radical $R_9$ is attached;

in the unsaturated cationic groups of formula (III):

when x=0, the linker arm D is attached to the nitrogen atom, when x=1, the linker arm D is attached to one of the ring members E, G, J, L and M, y can take the value 1 only when at least one of the ring members E, G, J, L and M is chosen from divalent atoms and when the radical $R_9$ is borne by the nitrogen atom of the unsaturated ring;

in the cationic groups of formula (IV):

when x=0, then the linker arm D is attached to the nitrogen atom bearing the radicals $R_{10}$ to $R_{12}$, when x=1, then two of the radicals $R_{10}$ to $R_{12}$ form, together with the nitrogen atom to which they are attached, a saturated 5- or 6-membered ring as defined above, and the linker arm D is borne by a carbon atom of the saturated ring;

$X^-$ is chosen from monovalent and divalent anions; it being understood that:

the number of cationic groups Z is at least equal to 1;

when at least one of $R_4$, $R_5$, $R'_4$, $R'_5$, $R_7$, $R_8$, $R'_7$, and $R'_8$ is chosen from Z groups in which the linker arm D is chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$;

when at least one of $R_4$, $R_5$, $R'_4$, $R'_5$, $R_7$, $R_8$, $R'_7$, and $R'_8$ is the point of a attachment of a linker arm B chosen from alkyl chains comprising a ketone function, then the ketone function is not directly attached to the nitrogen atom of the group —$NR_4R_5$, —$NR'_4R'_5$, —$NR_7R_8$ or —$NR'_7R'_8$.

* * * * *

UNITED STATES PATENT AND TRADEMARK OFFICE
CERTIFICATE OF CORRECTION

PATENT NO. : 6,379,398 B1
DATED : April 30, 2002
INVENTOR(S) : Alain Genet et al.

It is certified that error appears in the above-identified patent and that said Letters Patent is hereby corrected as shown below:

Column 18,
Line 50, after "Z groups;", insert a paragraph break.

Column 20,
Lines 38-39, before "$(C_1-C_6)$alkylcarboxy$(C_1-C_6)$alkyls", delete "a".

Column 21,
Line 22, "a attachment" should read -- an attachment --; and before "linker arm B", insert -- a --.
Lines 62-63, "1,3-bis{3-{3-[(2-aminoanilino)-N-propyl]}-3-H-imidazol-1-ium}propane" should read -- 1,3-bis{3-{3-[(2-aminoanilino)-N-propyl])-3H-imidazol-1-ium}propane --.
Lines 66-67, "1,4-bis{3-{2-[(2-aminoanilino)-N-ethyl]}-3-H-imidazol-1 ium}butane" should read --1,4-bis{3-{2-[(2-aminoanilino)-N-ethyl]}-3H-imidazol-1-ium}butane --.

Column 22,
Lines 40-41, "$C_1-C_6$)alkylcarboxyls" should read -- $(C_1-C_6)$alkylcarboxyls --.

Column 26,
Line 8; "a attachment" should read -- an attachment --.
Lines 48-49, "$(C_1-C_6)$alkylcarboxyls" should read -- $(C_1-C_6)$alkylcarboxyls --.
Line 61, "$(C_1-C_8)$alkoxy$(C_1-C_8)$alkyls" should read -- $(C_1-C_6)$alkoxy$(C_1-C_6)$alkyls --; and "$(C_1-C_5)$trifluoroalkyls" should read -- $(C_1-C_6)$trifluoroalkyls --.

Column 29,
Lines 30-31, "$(C_1-C_6)$trifluoroalkyl" should read -- $(C_1-C_6)$trifluoroalkyls; --.

Column 30,
Line 13, "a attachment" should read -- an attachment --.
Line 17, "-$NR_7R'_8$" should read -- -$NR'_7R'_8$ --.
Line 51, "2β-hydroxyethyloxy-para-phenylenediamine" should read -- 2-β-hydroxyethyloxy-para-phenylenediamine --.
Line 52, "2β-acetylaminoethyloxy-para-phenylenediamine" should read -- 2-β-acetylaminoethyloxy-para-phenylenediamine --.

Column 33,
Lines 1-2, "N-$(C_1-C_6)$alkylcarbamyl$(C_{1-96})$alkyls" should read -- N-$(C_1-C_6)$alkylcarbamyl$(C_1-C_6)$alkyls --.

UNITED STATES PATENT AND TRADEMARK OFFICE
CERTIFICATE OF CORRECTION

PATENT NO.   : 6,379,398 B1
DATED        : April 30, 2002
INVENTOR(S)  : Alain Genet et al.

It is certified that error appears in the above-identified patent and that said Letters Patent is hereby corrected as shown below:

<u>Column 34,</u>
Line 33, "NR'R'''" should read -- NR"R''' --.
Line 38, before "can be the point", insert -- $R_9$ --.

Lines 17-18, before "($C_1$-$C_6$)alkylcarboxy($C_1$-$C_6$)alkyls" delete "a".

<u>Column 35,</u>
Line 61, after "Z groups", insert -- in --.
Line 67, "a attachment" should read -- an attachment --.

<u>Column 36,</u>
Line 43, "arid" should read -- and --.
Lines 61-62, "$C_1$-$C_6$)alkylcarboxyls" should read -- ($C_1$-$C_6$)alkylcarboxyls --.

<u>Column 40,</u>
Line 40, "a attachment" should read -- an attachment --.

Signed and Sealed this

First Day of April, 2003

JAMES E. ROGAN
*Director of the United States Patent and Trademark Office*